United States Patent
Yamada et al.

(10) Patent No.: US 10,251,393 B2
(45) Date of Patent: *Apr. 9, 2019

(54) SYNTHETIC POLYMER FILM HAVING SURFACE PROVIDED WITH BACTERICIDAL ACTIVITY

(71) Applicant: Sharp Kabushiki Kaisha, Sakai, Osaka (JP)

(72) Inventors: Miho Yamada, Sakai (JP); Kiyoshi Minoura, Sakai (JP); Takahiro Nakahara, Sakai (JP); Ken Atsumo, Sakai (JP)

(73) Assignee: Sharp Kabushiki Kaisha, Sakai, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/126,078

(22) PCT Filed: Nov. 10, 2015

(86) PCT No.: PCT/JP2015/081608
§ 371 (c)(1),
(2) Date: Sep. 14, 2016

(87) PCT Pub. No.: WO2016/080245
PCT Pub. Date: May 26, 2016

(65) Prior Publication Data
US 2017/0258081 A1    Sep. 14, 2017

(30) Foreign Application Priority Data
Nov. 20, 2014   (JP) ................ 2014-236010

(51) Int. Cl.
| | | |
|---|---|---|
| B32B 3/30 | (2006.01) | |
| A01N 25/34 | (2006.01) | |
| A01N 59/00 | (2006.01) | |
| B32B 27/40 | (2006.01) | |
| C08J 5/18 | (2006.01) | |
| A01N 25/10 | (2006.01) | |
| A01N 33/12 | (2006.01) | |

(52) U.S. Cl.
CPC ............ *A01N 25/34* (2013.01); *A01N 25/10* (2013.01); *A01N 33/12* (2013.01); *A01N 59/00* (2013.01); *B32B 3/30* (2013.01); *B32B 27/40* (2013.01); *C08J 5/18* (2013.01)

(58) Field of Classification Search
None
See application file for complete search history.

(56) References Cited

U.S. PATENT DOCUMENTS

| | | |
|---|---|---|
| 2003/0164326 A1 | 9/2003 | Eberl et al. |
| 2003/0205475 A1 | 11/2003 | Sawitowski |
| 2007/0159698 A1 | 7/2007 | Taguchi et al. |
| 2009/0252825 A1 | 10/2009 | Taguchi et al. |
| 2010/0009137 A1 | 1/2010 | Kodama |
| 2010/0203161 A1 | 8/2010 | Gehri et al. |
| 2010/0234323 A1* | 9/2010 | Holzl ............. A01N 37/04 514/63 |
| 2011/0235181 A1 | 9/2011 | Hayashibe et al. |
| 2011/0281068 A1 | 11/2011 | David et al. |
| 2012/0318772 A1 | 12/2012 | Minoura et al. |
| 2013/0057958 A1 | 3/2013 | Minoura et al. |
| 2013/0344290 A1 | 12/2013 | Yu et al. |
| 2014/0004304 A1 | 1/2014 | Yu et al. |
| 2014/0077418 A1 | 3/2014 | Otani et al. |
| 2015/0140154 A1 | 5/2015 | Isurugi et al. |
| 2015/0168610 A1 | 6/2015 | Fukui et al. |
| 2015/0273755 A1 | 10/2015 | Yee et al. |
| 2016/0212989 A1 | 7/2016 | Juodkazis et al. |

FOREIGN PATENT DOCUMENTS

| | | |
|---|---|---|
| CN | 201329050 Y | 10/2009 |
| EP | 2979844 A1 | 2/2016 |
| JP | 08-024843 A | 1/1996 |
| JP | 2005-055114 A | 3/2005 |
| JP | 2008-197217 A | 8/2008 |
| JP | 4265729 A | 2/2009 |
| JP | 2009-166502 A | 7/2009 |
| JP | 2010-000719 A | 1/2010 |
| JP | 2010-079200 A | 4/2010 |
| JP | 2012-078438 A | 4/2012 |
| JP | 2012-514239 | 6/2012 |
| JP | 2012-514239 A | 6/2012 |
| JP | 2012-208169 A | 10/2012 |
| JP | 2013-033287 A | 2/2013 |

(Continued)

OTHER PUBLICATIONS

Pogodin, Sergey, et al. "Biophysical model of bacterial cell interactions with nanopatterned cicada wing surfaces." Biophysical journal 104.4 (2013): 835-840.*
Espeel, Pieter, et al. "One-pot, additive-free preparation of functionalized polyurethanes via amine-thiol-ene conjugation." Polymer Chemistry 4.8 (2013): 2449-2456.*
Compound Summary for CID 3086063, Tecoflex from PubChem, accessed Jan. 17, 2018.*
Mao, H. Y., et al. "Fabrication of nanopillars based on silicon oxide nanopatterns synthesized in oxygen plasma removal of photoresist." Micro Electro Mechanical Systems, 2009. MEMS 2009. IEEE 22nd International Conference on. IEEE, 2009. (Year: 2009).*

(Continued)

*Primary Examiner* — Nissa M Westerberg
(74) *Attorney, Agent, or Firm* — Harness, Dickey & Pierce, P.L.C.

(57) ABSTRACT

A synthetic polymer film includes a surface which has a plurality of raised portions. A two-dimensional size of the plurality of raised portions is in a range of more than 20 nm and less than 500 nm when viewed in a normal direction of the synthetic polymer film. The surface has a microbicidal effect. Further, a concentration of a nitrogen element included in the surface is not less than 0.7 at %.

9 Claims, 12 Drawing Sheets

(56) References Cited

FOREIGN PATENT DOCUMENTS

| | | |
|---|---|---|
| JP | 2013-078573 A | 5/2013 |
| JP | 2014-029391 A | 2/2014 |
| JP | 2014-066975 A | 4/2014 |
| JP | 2014-509967 A | 4/2014 |
| JP | 2014-511779 | 5/2014 |
| JP | 2014-511779 A | 5/2014 |
| JP | 2014-202955 A | 10/2014 |
| JP | 2015-024549 A | 2/2015 |
| WO | WO-2007/097454 A1 | 8/2007 |
| WO | WO-2011/125486 A1 | 10/2011 |
| WO | WO-2011/148721 A1 | 12/2011 |
| WO | WO-2012/161315 A1 | 11/2012 |
| WO | WO-2013/183576 A1 | 12/2013 |
| WO | WO-2013/191092 A1 | 12/2013 |
| WO | WO-2014/021376 A1 | 2/2014 |
| WO | WO-2014/171365 A1 | 10/2014 |
| WO | WO-2015/163018 A1 | 10/2015 |

OTHER PUBLICATIONS

Jeong, Hoon Eui, and Kahp-Yang Suh. "Precise tip shape transformation of nanopillars for enhanced dry adhesion strength." Soft Matter 8.19 (2012): 5375-5380. (Year: 2012).*
International Search Report PCT/ISA/210 for International Application No. PCT/JP2015/081608 dated Feb. 3, 2016.
International Search Report PCT/ISA/210 for International Application No. PCT/JP2015/057327 dated Jun. 3, 2015.
E. P. Ivanova, "Bactericidal activity of black silicon", Nature Communications, Published Nov. 26, 2013, 19 pgs, Macmillan Publishers Limited.
Epstein, A.K. et al. "Liquid-infused structured surfaces with exceptional anti-biofouling performance," PNAS, Aug. 14, 2012, vol. 109, No. 33.
Yao, C. et al., "Decreased bacteria density on nanostructured polyurethane," Society for Biomaterials, pp. 1823-18-28, Jun. 29, 2013.
Ivanova, E. et al., "Natural Bactericidal Surfaces: Mechanical Rupture of Pseudomonas aeruginosa Cells by Cicada Wings," Small Journal, pp. 1-6, 2012.
Office Action dated Dec. 29, 2016 issued in U.S. Appl. No. 14/771,833.
Office Action dated Mar. 9, 2017 issued in U.S. Appl. No. 15/386,131.
Office Action dated Oct. 27, 2016 issued in U.S. Appl. No. 14/771,833.
Trafton, A., (2006) "MIT's Anti-Microbial 'Paint' Kills Flu, Bacteria" http://chemistry.mit.edu/mits-anti-microbial-paint-kills-flu-bacteria, p. 2-4.
Good Housekeeping (2011) "Do-It-All Cleaning Guide" http://www.goodhousekeeping.com/home/cleaning/tips/a18875/how-to-clean/, p. 1-12.
Office Action dated Apr. 13, 2018 issued in U.S. Appl. No. 14/897,252.
Office Action dated Dec. 11, 2017 issued in U.S. Appl. No. 15/592,922.
Office Action dated Nov. 24, 2017 issued in U.S. Appl. No. 14/897,252.
U.S. Appl. No. 14/771,833, filed Sep. 1, 2015.
U.S. Appl. No. 14/897,252, filed Dec. 10, 2015.

* cited by examiner (a)

(b)

(c)

(a)

(b)

(a)

1.00μm (b)

500nm (a)

(b)

(a)

(b)

(c)

SYNTHETIC POLYMER FILM HAVING SURFACE PROVIDED WITH BACTERICIDAL ACTIVITY

TECHNICAL FIELD

The present invention relates to a synthetic polymer film whose surface has a microbicidal activity, a sterilization method with the use of the surface of the synthetic polymer film, a mold for production of the synthetic polymer film, and a mold manufacturing method. In this specification, the "mold" includes molds that are for use in various processing methods (stamping and casting), and is sometimes referred to as a stamper. The "mold" can also be used for printing (including nanoimprinting).

BACKGROUND ART

Recently, it was reported that surficial nanostructures of black silicon, wings of cicadas and dragonflies have a bactericidal activity (Non-patent Document 1). Reportedly, the physical structure of the nanopillars that black silicon and wings of cicadas and dragonflies have produces a bactericidal activity.

According to Non-patent Document 1, black silicon has the strongest bactericidal activity on Gram-negative bacteria, while wings of dragonflies have a weaker bactericidal activity, and wings of cicadas have a still weaker bactericidal activity. Black silicon has 500 nm tall nanopillars. Wings of cicadas and dragonflies have 240 nm tall nanopillars. The static contact angle (hereinafter, sometimes simply referred to as "contact angle") of the black silicon surface with respect to water is 80°, while the contact angles of the surface of wings of dragonflies and cicadas with respect to water are 153° and 159°, respectively. It is estimated that black silicon is mainly made of silicon, and wings of dragonflies and cicadas are made of chitin. According to Non-patent Document 1, the composition of the surface of black silicon is generally a silicon oxide, and the composition of the surface of wings of dragonflies and cicadas is generally a lipid.

CITATION LIST

Patent Literature

Patent Document 1: Japanese Patent No. 4265729
Patent Document 2: Japanese Laid-Open Patent Publication No. 2009-166502
Patent Document 3: WO 2011/125486
Patent Document 4: WO 2013/183576

Non-Patent Literature

Non-patent Document 1: Ivanova, E. P. et al., "Bactericidal activity of black silicon", Nat. Commun. 4:2838 doi: 10.1038/ncomms3838 (2013).

SUMMARY OF INVENTION

Technical Problem

The mechanism of killing bacteria by nanopillars is not clear from the results described in Non-patent Document 1. It is also not clear whether the reason why black silicon has a stronger bactericidal activity than wings of dragonflies and cicadas resides in the difference in height or shape of nanopillars, in the difference in surface free energy (which can be evaluated by the contact angle), in the materials that constitute nanopillars, or in the chemical properties of the surface.

The bactericidal activity of black silicon is difficult to utilize because black silicon is poor in mass productivity, and is hard but brittle so that the shapability is poor.

The present invention was conceived for the purpose of solving the above problems. The major objects of the present invention include providing a synthetic polymer film whose surface has a microbicidal activity, a sterilization method with the use of the surface of the synthetic polymer film, a mold for production of the synthetic polymer film, and a mold manufacturing method.

Solution to Problem

A synthetic polymer film according to an embodiment of the present invention is a synthetic polymer film having a surface which has a plurality of raised portions, wherein a two-dimensional size of the plurality of raised portions is in a range of more than 20 nm and less than 500 nm when viewed in a normal direction of the synthetic polymer film, the surface having a microbicidal effect, and a concentration of a nitrogen element included in the surface is not less than 0.7 at %.

In one embodiment, the synthetic polymer film includes a urethane resin.

In one embodiment, the number of functional groups included in the urethane resin is less than 10.

In one embodiment, the number of functional groups included in the urethane resin is less than 6.

In one embodiment, the synthetic polymer film includes any of an amino group, an isocyanate group and a cyano group. The synthetic polymer film may include any of an amino group, an isocyanate group and a cyano group in the surface.

In one embodiment, the synthetic polymer film includes a compound whose terminal functional group is —$NH_2$ or —NHR (where R represents a hydrocarbon group).

In one embodiment, the synthetic polymer film includes a coupling agent which includes any of an amino group, an isocyanate group and a cyano group.

In one embodiment, the synthetic polymer film includes the coupling agent in the surface, a concentration of a nitrogen atom included in the coupling agent being not less than 0.7 at %.

In one embodiment, the synthetic polymer film includes an alkali metal salt or an alkali earth metal salt.

In one embodiment, the synthetic polymer film includes a lithium salt.

A synthetic polymer film according to another embodiment of the present invention is a synthetic polymer film having a surface which has a plurality of raised portions, wherein a two-dimensional size of the plurality of raised portions is in a range of more than 20 nm and less than 500 nm when viewed in a normal direction of the synthetic polymer film, the surface having a microbicidal effect, and a concentration of a sulfur element included in the surface is not less than 3.7 at %.

In one embodiment, the synthetic polymer film includes a mercapto group. The synthetic polymer film may include a mercapto group in the surface.

In one embodiment, the synthetic polymer film includes a compound whose terminal functional group is —SH.

In one embodiment, the synthetic polymer film includes a coupling agent which includes a mercapto group.

In one embodiment, the synthetic polymer film includes the coupling agent in the surface, a concentration of a sulfur element included in the coupling agent being not less than 3.7 at %.

A synthetic polymer film according to still another embodiment of the present invention is a synthetic polymer film including a surface which has a plurality of first raised portions, wherein a two-dimensional size of the plurality of first raised portions is in a range of more than 20 nm and less than 500 nm when viewed in a normal direction of the synthetic polymer film; and the surface has a microbicidal effect.

In one embodiment, an adjoining distance of the plurality of first raised portions is more than 20 nm and not more than 1000 nm.

In one embodiment, a height of the plurality of first raised portions is not less than 50 nm and less than 500 nm. The height of the plurality of first raised portions may be not more than 150 nm.

In one embodiment, the synthetic polymer film further includes a plurality of second raised portions superimposedly formed over the plurality of first raised portions, wherein a two-dimensional size of the plurality of second raised portions is smaller than the two-dimensional size of the plurality of first raised portions and does not exceed 100 nm.

In one embodiment, the plurality of second raised portions include a generally conical portion.

In one embodiment, a height of the plurality of second raised portions is more than 20 nm and not more than 100 nm.

A method for sterilizing a gas or liquid according to an embodiment of the present invention includes bringing the gas or liquid into contact with the surface of any of the above-described synthetic polymer films.

A mold according to an embodiment of the present invention includes a surface, the surface having a plurality of first recessed portions and a plurality of second recessed portions formed in the plurality of first recessed portions, wherein a two-dimensional size of the plurality of first recessed portions is in a range of more than 20 nm and less than 500 nm when viewed in a normal direction of the surface of the mold, and a two-dimensional size of the plurality of second recessed portions is smaller than the two-dimensional size of the plurality of first recessed portions and does not exceed 100 nm.

A mold manufacturing method according to an embodiment of the present invention is a method for manufacturing the above-described mold, including: (a) a step of providing an aluminum base or an aluminum film deposited on a support; (b) an anodization step of applying a voltage at a first level while a surface of the aluminum base or the aluminum film is kept in contact with an electrolytic solution, thereby forming a porous alumina layer which has first recessed portions; (c) after step (b), an etching step of bringing the porous alumina layer into contact with an etching solution, thereby enlarging the first recessed portions; and (d) after step (c), applying a voltage at a second level which is lower than the first level while the porous alumina layer is kept in contact with an electrolytic solution, thereby forming second recessed portions in the first recessed portions.

In one embodiment, the first level is higher than 40 V, and the second level is equal to or lower than 20 V.

In one embodiment, the electrolytic solution is an oxalic acid aqueous solution.

Advantageous Effects of Invention

According to an embodiment of the present invention, a synthetic polymer film whose surface has a microbicidal activity, a sterilization method with the use of the surface of the synthetic polymer film, a mold for production of the synthetic polymer film, and a mold manufacturing method are provided.

DESCRIPTION OF EMBODIMENTS

Hereinafter, a synthetic polymer film whose surface has a microbicidal effect, a sterilization method with the use of the surface of the synthetic polymer film, a mold for production of the synthetic polymer film, and a mold manufacturing method according to embodiments of the present invention are described with reference to the drawings.

In this specification, the following terms are used.

"Sterilization" (or "microbicidal") means reducing the number of proliferative microorganisms contained in an object, such as solid or liquid, or a limited space, by an effective number.

"Microorganism" includes viruses, bacteria, and fungi.

"Antimicrobial" generally includes suppressing and preventing multiplication of microorganisms and includes suppressing dinginess and slime which are attributed to microorganisms.

The present applicant conceived a method for producing an antireflection film (an antireflection surface) which has a moth-eye structure with the use of an anodized porous alumina layer. Using the anodized porous alumina layer enables manufacture of a mold which has an inverted moth-eye structure with high mass-productivity (e.g., Patent Documents 1 to 4). The entire disclosures of Patent Documents 1 to 4 are incorporated by reference in this specification. Note that antireflection films which are placed over the surface of liquid crystal television displays manufactured and sold until now by the present applicant are hydrophilic. This is for the purpose of facilitating wiping away of grease, such as fingerprint, adhered to the moth-eye structure. If the moth-eye structure is not hydrophilic, an aqueous washing solution cannot effectively enter the gap between raised portions of the moth-eye structure so that the grease cannot be wiped away.

The present inventors developed the above-described technology and arrived at the concept of a synthetic polymer film whose surface has a microbicidal effect.

The configuration of a synthetic polymer film according to an embodiment of the present invention is described with reference to FIGS. 1(*a*) and 1(*b*).

Figure 1:
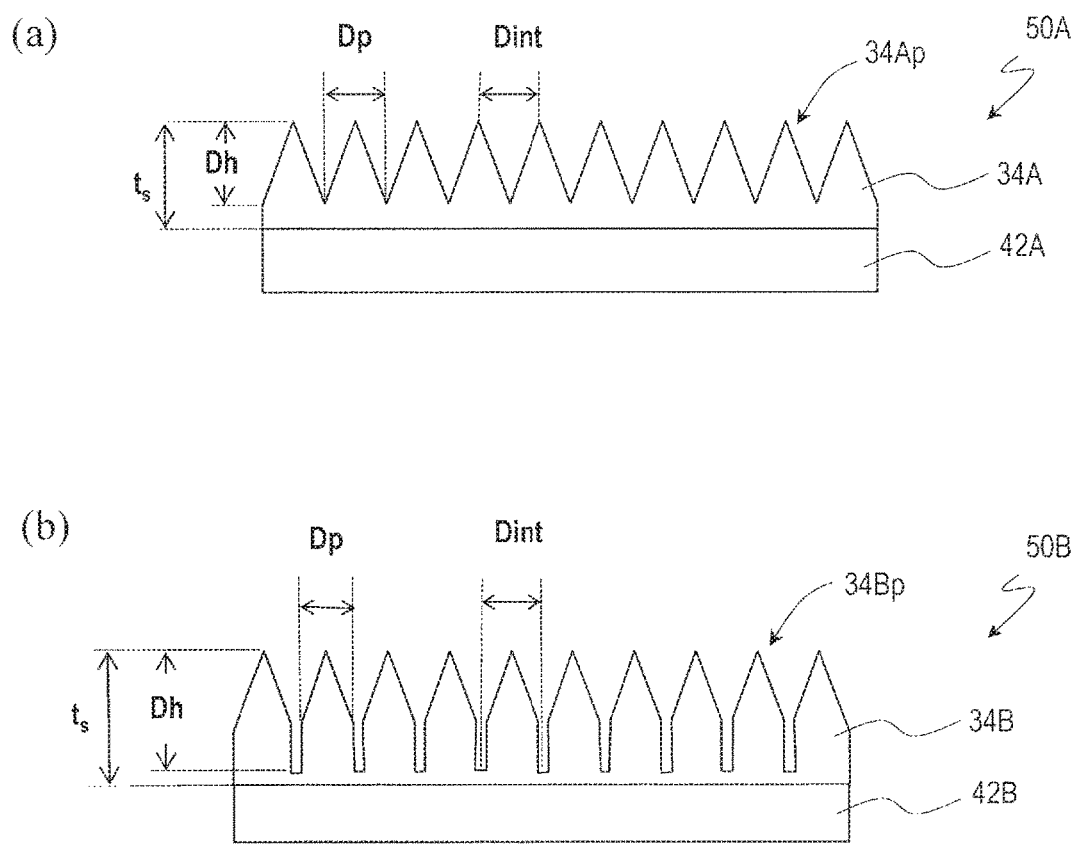
FIGS. 1 (a) and (b) are schematic cross-sectional views of synthetic polymer films 34A and 34B, respectively, according to embodiments of the present invention.

FIGS. 1(*a*) and 1(*b*) respectively show schematic cross-sectional views of synthetic polymer films 34A and 34B according to embodiments of the present invention. The synthetic polymer films 34A and 34B described herein as examples are formed on base films 42A and 42B, respectively, although the present invention is not limited to these examples. The synthetic polymer films 34A and 34B can be directly formed on a surface of an arbitrary object.

A film 50A shown in FIG. 1(*a*) includes a base film 42A and a synthetic polymer film 34A provided on the base film 42A. The synthetic polymer film 34A has a plurality of raised portions 34Ap over its surface. The plurality of raised portions 34Ap constitute a moth-eye structure. When viewed in a normal direction of the synthetic polymer film 34A, the two-dimensional size of the raised portions 34Ap, $D_p$, is in the range of more than 20 nm and less than 500 nm. Here, the "two-dimensional size" of the raised portions 34Ap refers to the diameter of a circle equivalent to the area of the raised portions 34Ap when viewed in a normal direction of the surface. When the raised portions 34Ap have a conical shape, for example, the two-dimensional size of the raised portions 34Ap is equivalent to the diameter of the base of the cone. The typical adjoining distance of the raised portions 34Ap, $D_{int}$, is more than 20 nm and not more than 1000 nm. When the raised portions 34Ap are densely arranged so that there is no gap between adjoining raised portions 34Ap (e.g., the bases of the cones partially overlap each other) as shown in FIG. 1(*a*), the two-dimensional size of the raised portions 34Ap, $D_p$, is equal to the adjoining distance $D_{int}$. The typical height of the raised portions 34Ap, $D_h$, is not less than 50 nm and less than 500 nm. As will be described later, a microbicidal activity is exhibited even when the height D of the raised portions 34Ap is not more than 150 nm. The thickness of the synthetic polymer film 34A, $t_s$, is not particularly limited but only needs to be greater than the height $D_n$ of the raised portions 34Ap.

The surface of the synthetic polymer film 34A has a microbicidal ability. The concentration of the nitrogen element included in the surface of the synthetic polymer film 34A is not less than 0.7 at %. As will be described later with experimental examples, the synthetic polymer film 34A has an excellent microbicidal effect due to the physical structure of the surface of the synthetic polymer film 34A (raised portions 34Ap) and the chemical properties of the surface of the synthetic polymer film 34A which includes the nitrogen element. As will be described later with reference to FIGS. 8(*a*) and 8(*b*), for example, it is estimated that the raised portions 34Ap break, for example, the cell walls of *Pseudomonas aeruginosa* (or "*P. aeruginosa*") that is one of the Gram-negative bacteria, thereby killing *P. aeruginosa* bacteria. In this case, a more excellent microbicidal effect is achieved due to the chemical properties of the surface of the synthetic polymer film 34A. Details will be described later.

As will be described later, the surface of the synthetic polymer film 34A may include the sulfur element in a proportion of not less than 3.7 at % instead of including the nitrogen element in a proportion of not less than 0.7 at %. As a matter of course, the surface of the synthetic polymer film 34A may include the nitrogen element in a proportion of not less than 0.7 at % and the sulfur element in a proportion of not less than 3.7 at %.

The synthetic polymer film 34A shown in FIG. 1(*a*) has the same moth-eye structure as the antireflection films disclosed in Patent Documents 1 to 4. From the viewpoint of producing an antireflection function, it is preferred that the surface has no flat portion, and the raised portions 34Ap are densely arranged over the surface. Further, the raised portions 34Ap preferably has a such shape that the cross-sectional area (a cross section parallel to a plane which is orthogonal to an incoming light ray, e.g., a cross section parallel to the surface of the base film 42A) increases from the air side to the base film 42A side, e.g., a conical shape. From the viewpoint of suppressing interference of light, it is preferred that the raised portions 34Ap are arranged without regularity, preferably randomly. However, these features are unnecessary when only the microbicidal activity of the synthetic polymer film 34A is pursued. For example, the raised portions 34Ap do not need to be densely arranged. The raised portions 34Ap may be regularly arranged. Note that, however, the shape and arrangement of the raised portions 34Ap are preferably selected such that the raised portions 34Ap effectively act on microorganisms.

A film 50B shown in FIG. 1(*b*) includes a base film 42B and a synthetic polymer film 34B provided on the base film 42B. The synthetic polymer film 34B has a plurality of raised portions 34Bp over its surface. The plurality of raised portions 34Bp constitute a moth-eye structure. In the film 50B, the configuration of the raised portions 34Bp of the synthetic polymer film 34B is different from that of the raised portions 34Ap of the synthetic polymer film 34A of the film 50A. Descriptions of features which are common with those of the film 50A are sometimes omitted.

When viewed in a normal direction of the synthetic polymer film 34B, the two-dimensional size of the raised portions 34Bp, $D_p$, is in the range of more than 20 nm and less than 500 nm. The typical adjoining distance of the raised portions 34Bp, $D_{int}$, is more than 20 nm and not more than 1000 nm, and $D_p < D_{int}$ holds. That is, in the synthetic polymer film 34B, there is a flat portion between adjoining raised portions 34Bp. The raised portions 34Bp have the shape of a cylinder with a conical portion on the air side. The typical height of the raised portions 34Bp, $D_h$, is not less than 50 nm and less than 500 nm. The raised portions 34Bp may be arranged regularly or may be arranged irregularly. When the raised portions 34Bp are arranged regularly, $D_{int}$ also represents the period of the arrangement. This also applies to the synthetic polymer film 34A, as a matter of course.

In this specification, the "moth-eye structure" includes not only surficial nanostructures that have an excellent antireflection function and that are formed by raised portions which have such a shape that the cross-sectional area (a cross section parallel to the film surface) increases as do the raised portions 34Ap of the synthetic polymer film 34A shown in FIG. 1(a) but also surficial nanostructures that are formed by raised portions which have a part where the cross-sectional area (a cross section parallel to the film surface) is constant as do the raised portions 34Bp of the synthetic polymer film 34B shown in FIG. 1(b). Note that, from the viewpoint of breaking the cell walls and/or cell membranes of microorganisms, providing a conical portion is preferred. Note that, however, the tip end of the conical shape does not necessarily need to be a surficial nanostructure but may have a rounded portion (about 60 nm) which is generally equal to the nanopillars which form surficial nanostructures of the wings of cicadas.

As will be described later with experimental examples, the microbicidal ability of the synthetic polymer films 34A and 34B has not only a correlation with the physical structure of the synthetic polymer films 34A and 34B but also a correlation with the chemical properties of the synthetic polymer films 34A and 34B. Here, the chemical properties of a synthetic polymer film refer to, for example, the composition of the synthetic polymer film, the constituents of the synthetic polymer film, and the functional groups of the compounds (including polymer compounds and low molecular weight compounds) included in the synthetic polymer film. According to the research conducted by the present inventors, in order that the synthetic polymer films 34A and 34B have an excellent microbicidal ability, it is preferred that the synthetic polymer films 34A and 34B have any of the chemical properties which will be described below.

Note that, although an example of forming a synthetic polymer film with the use of a UV-curable resin (e.g., an acrylic resin (including a methacrylic resin)) is illustrated herein, the same applies to cases where other photocurable resins, thermosetting resins, and electron beam curable resins are used.

First Chemical Property: The concentration of the nitrogen element (N) included in the surface of the synthetic polymer films 34A and 34B is preferably not less than 0.7 at %.

The concentration of the nitrogen element included in the surface of the synthetic polymer films 34A and 34B can be controlled by selection of the resin material that forms the synthetic polymer films 34A and 34B and can also be controlled by mixing a plurality of resin materials. Also, it can be controlled by adding a material which includes a nitrogen element (e.g., a surface treatment agent which will be described below) to the resin material. Some of these options can be used in combination.

When synthetic polymer films are formed using a resin material (including a mixture) in which the thus-controlled concentration of the nitrogen element is not less than 0.7 at %, the concentration of the nitrogen element included in the synthetic polymer films 34A and 34B is not less than 0.7 at %. If such a resin material is evenly used, the concentration of the nitrogen element included in the surface of the synthetic polymer films 34A and 34B can be not less than 0.7 at %.

Even when the concentration of the nitrogen element included in the resin material (including a mixture) that forms the synthetic polymer films 34A and 34B is less than 0.7 at %, the surface of the synthetic polymer films 34A and 34B can be treated such that the concentration of the nitrogen element included in the surface of the synthetic polymer films 34A and 34B is not less than 0.7 at %.

For example, a surface treatment agent (including, for example, a silane coupling agent, a mold releasing agent, and an antistatic agent) may be applied over the surface of the synthetic polymer films 34A and 34B. Some types of the surface treatment agents cause formation of a thin polymer film over the surface of the synthetic polymer films 34A and 34B. Alternatively, the surface of the synthetic polymer films 34A and 34B may be modified using plasma or the like. For example, a functional group including a nitrogen element or a nitrogen element can be applied to the surface of the synthetic polymer films 34A and 34B by a plasma treatment.

The above-described surface treatment may be provided together with or independently of selection of the resin material (including a mixture) that forms the synthetic polymer films 34A and 34B.

The synthetic polymer films 34A and 34B include, for example, a urethane resin. The synthetic polymer films 34A and 34B include, for example, urethane (meth)acrylate, cyano (meth)acrylate, or the like. The number of functional groups included in the urethane resin is preferably less than 10, for example. The number of functional groups included in the urethane resin is more preferably less than 6, for example. When the urethane resin includes a large number of functional groups, the viscosity of the resin is high in some cases. In such a case, the resin is sometimes unlikely to fill the inverted moth-eye structure at the surface of a moth-eye mold (a mold for formation of a moth-eye structure in a surface). As a result, the antireflection function of an antireflection film to be formed sometimes deteriorates (deterioration of transferability). To avoid this problem, i.e., to decrease the viscosity of the resin, for example, the molecular weight of monomers in the resin can be reduced. When the molecular weight of monomers is reduced, the crosslink density of the resin increases, and accordingly, it is more difficult to peel off (separate) a formed antireflection film from the moth-eye mold (deterioration of mold releasability). When the mold releasability of the antireflection film deteriorates, the resin (part of the film) remains in the inverted moth-eye structure at the surface of the moth-eye mold, and/or an object which has the resin over its surface (e.g., the base films 42A and 42B of FIG. 1) breaks.

The synthetic polymer films 34A and 34B preferably include any of an amino group (—NH$_2$, —NHR, or —NRR':

R and R' each represent a hydrocarbon group), an isocyanate group (—N=C=O), and a cyano group (—C≡N).

The synthetic polymer films 34A and 34B may include a polymer compound which has any of the aforementioned functional groups or may include a surface treatment agent (including, for example, a silane coupling agent, a mold releasing agent, and an antistatic agent) which includes any of the aforementioned functional groups. The polymer compound or surface treatment agent may include a compound in which any of the aforementioned functional groups is bonded to another functional group through a reaction. The surface treatment agent may be applied over the surface of the synthetic polymer films 34A and 34B or may be mixed into monomers that form the synthetic polymer films 34A and 34B.

The synthetic polymer films 34A and 34B preferably include a compound (including a polymer compound and a surface treatment agent) which includes any of an amino group (—$NH_2$, —NHR, or —NRR': R and R' each represent a hydrocarbon group), an isocyanate group (—N=C=O), and a cyano group (—C≡N) in the terminal functional group. More preferably, the synthetic polymer films 34A and 34B include a compound which has —$NH_2$ or —NHR (R represents a hydrocarbon group) in the terminal functional group. The synthetic polymer films 34A and 34B may include a polymer which includes NH at the main chain.

The synthetic polymer films 34A and 34B may include an alkali metal salt (including, for example, lithium (Li) salt, sodium (Na) salt, and potassium (K) salt) or an alkali earth metal salt (e.g., calcium (Ca) salt) or a magnesium salt. The synthetic polymer films 34A and 34B may include, for example, a quaternary ammonium salt. When including these salts (including metal salts), the synthetic polymer films 34A and 34B can have a more excellent microbicidal ability.

The synthetic polymer films 34A and 34B may be made of a polymer which includes, for example, an alkali metal salt, alkali earth metal salt, magnesium salt, or quaternary ammonium salt. For example, a known antistatic agent or conducting agent may be used as such a polymer. Among alkali metal salts, examples of lithium salts include $LiBF_4$, $LiClO_4$, $LiPF_6$, $LiAsF_6$, $LiSbF_6$, $LiSO_3CF_3$, $LiN(SO_2CF_3)_2$, $LiSO_3C_4F_9$, $LiC(SO_7CF_3)_3$, and $LiB(C_6H_5)_4$.

In the synthetic polymer films 34A and 34B, the salts listed above (including metal salts) may be present in the form of a cation (alkali metal ion, alkali earth metal ion, magnesium ion, or quaternary ammonium cation). Preferably, the synthetic polymer films 34A and 34B further include, for example, a polymer which has an ether bond (e.g., polyethylene oxide) and/or a lubricant.

Second Chemical Property: The concentration of the sulfur element (S) included in the surface of the synthetic polymer films 34A and 34B is not less than 3.7 at %.

For example, the synthetic polymer film preferably includes a mercapto group (—SH). The synthetic polymer film may include a polymer compound which has a mercapto group or may include a surface treatment agent (including, for example, a silane coupling agent and a mold releasing agent) which includes a mercapto group. The surface treatment agent may be applied over the surface of the synthetic polymer film or may be mixed into monomers that form the synthetic polymer film. The synthetic polymer film preferably includes a compound which has —SH in the terminal functional group.

The synthetic polymer film may be made of, for example, an acrylic resin which includes copper sulfide.

The synthetic polymer film may have either one or both of the first and second chemical properties described above.

The present inventors examined the reason why the synthetic polymer film has an excellent microbicidal effect when it has the first or second chemical property described above.

Nitrogen element (N) has the electron configuration of $(1s)^2(2s)^2(2p)^3$ and has five valence electrons. Three of these valence electrons are unpaired electrons and have one lone pair (unshared pair). For example, the nitrogen element of an amino group also has one lone pair. The amino group is capable of forming a coordinate bond with a hydrogen ion ($H^+$) because the nitrogen element has a lone pair. Therefore, the amino group exhibits properties as a base. Likewise, an amino group which has a lone pair has nucleophilicity. A compound which includes an amino group which has a lone pair functions as a ligand and is capable of forming a coordinate bond with a metal.

Thus, a compound which includes a nitrogen element (including a compound which has a functional group which includes a nitrogen element) can have a characteristic which is attributed to a lone pair included in the nitrogen element. Not only in the above-described amino group but also in a cyano group (—C≡N), for example, the nitrogen element has one lone pair. In an isocyanate group (—N=C=O), the nitrogen element has one lone pair, and the oxygen element has two lone pairs. In a ureido group (—NHC(=O)$NH_2$) that is a functional group which includes an amino group, each of the nitrogen elements has one lone pair, and the oxygen element has two lone pairs.

Nitrogen element has relatively large electronegativity and therefore strongly attracts electrons when it forms a bond (including a coordinate bond) with another element. That is, a molecule in which a nitrogen element forms a bond (including a coordinate bond) with another element is a polar molecule in many cases.

It is estimated that there is a probability that the reason why a synthetic polymer film which includes a nitrogen element in its surface has an excellent microbicidal ability is attributed to the above-described features of having the lone pair and having large electronegativity. These features also apply to sulfur element. Sulfur element has six valence electrons and has two lone pairs.

From the viewpoint of the foregoing, the synthetic polymer film of an embodiment of the present invention is not limited to synthetic polymer films which have the first or second chemical property described above. The synthetic polymer film of an embodiment of the present invention is not limited to the nitrogen element or the sulfur element but may have any of Group 15 elements, Group 16 elements, and Group 17 elements in its surface. Group 15 elements (e.g., nitrogen element (N), phosphorus element (P)) have one lone pair. Group 16 elements (e.g., oxygen element (O), sulfur element (S)) have two lone pairs. Group 17 elements (e.g., fluorine element (F), chlorine element (Cl)) have three lone pairs. Some of these elements which have smaller atomic numbers (e.g., F, O, N, Cl, S, P) are particularly preferred because they have large electronegativity.

As disclosed in Japanese Patent No. 5788128 of the present applicant, synthetic polymer films which are made of a fluorine-containing acrylic resin or an urethane acrylate-containing acrylic resin to which a fluoric lubricant is added, and which have a moth-eye structure over the surface, were found to have a microbicidal ability. It can also be considered that the reason why these synthetic polymer films have a microbicidal effect is attributed to the feature of including a fluorine element, which has three lone pairs and has large electronegativity, in the surface.

A mold for forming the moth-eye structure such as illustrated in FIGS. 1(a) and 1(b) over the surface (hereinafter, referred to as "moth-eye mold") has an inverted moth-eye structure obtained by inverting the moth-eye structure. Using an anodized porous alumina layer which has the inverted moth-eye structure as a mold without any modification enables inexpensive production of the moth-eye structure. Particularly when a moth-eye mold in the shape of a hollow cylinder is used, the moth-eye structure can be efficiently manufactured according to a roll-to-roll method. Such a moth-eye mold can be manufactured according to methods disclosed in Patent Documents 2 to 4.

A manufacturing method of a moth-eye mold 100A that is for production of the synthetic polymer film 34A is described with reference to FIGS. 2(a) to 2(e).

Firstly, a mold base 10 is provided which includes an aluminum base 12, an inorganic material layer 16 provided on a surface of the aluminum base 12, and an aluminum film 18 deposited on the inorganic material layer 16 as shown in FIG. 2(a).

The aluminum base 12 used may be an aluminum base whose aluminum purity is not less than 99.50 mass % and less than 99.99 mass % and which has relatively high rigidity. The impurity contained in the aluminum base 12 may preferably include at least one element selected from the group consisting of iron (Fe), silicon (Si), copper (Cu), manganese (Mn), zinc (Zn), nickel (Ni), titanium (Ti), lead (Pb), tin (Sn) and magnesium (Mg). Particularly, Mg is preferred. Since the mechanism of formation of pits (hollows) in the etching step is a local cell reaction, the aluminum base 12 ideally does not contain any element which is nobler than aluminum. It is preferred that the aluminum base 12 used contains, as the impurity element, Mg (standard electrode potential: −2.36 V) which is a base metal. If the content of an element nobler than aluminum is 10 ppm or less, it can be said in terms of electrochemistry that the aluminum base 12 does not substantially contain the element. The Mg content is preferably 0.1 mass % or more of the whole. It is, more preferably, in the range of not more than about 3.0 mass %. If the Mg content is less than 0.1 mass %, sufficient rigidity cannot be obtained. On the other hand, as the Mg content increases, segregation of Mg is more likely to occur. Even if the segregation occurs near a surface over which a moth-eye mold is to be formed, it would not be detrimental in terms of electrochemistry but would be a cause of a defect because Mg forms an anodized film of a different form from that of aluminum. The content of the impurity element may be appropriately determined depending on the shape, thickness, and size of the aluminum base 12, in view of required rigidity. For example, when the aluminum base 12 in the form of a plate is prepared by rolling, the appropriate Mg content is about 3.0 mass %. When the aluminum base 12 having a three-dimensional structure of, for example, a hollow cylinder is prepared by extrusion, the Mg content is preferably 2.0 mass % or less. If the Mg content exceeds 2.0 mass %, the extrudability deteriorates in general.

The aluminum base 12 used may be an aluminum pipe in the shape of a hollow cylinder which is made of, for example, JIS A1050, an Al—Mg based alloy (e.g., JIS A5052), or an Al—Mg—Si based alloy (e.g., JIS A6063).

The surface of the aluminum base 12 is preferably a surface cut with a bit. If, for example, abrasive particles are remaining on the surface of the aluminum base 12, conduction will readily occur between the aluminum film 18 and the aluminum base 12 in a portion in which the abrasive particles are present. Not only in the portion in which the abrasive particles are remaining but also in a portion which has a roughened surface, conduction readily occurs between the aluminum film 18 and the aluminum base 12. When conduction occurs locally between the aluminum film 18 and the aluminum base 12, there is a probability that a local cell reaction will occur between an impurity in the aluminum base 12 and the aluminum film 18.

The material of the inorganic material layer 16 may be, for example, tantalum oxide ($Ta_2O_5$) or silicon dioxide ($SiO_2$). The inorganic material layer 16 can be formed by, for example, sputtering. When a tantalum oxide layer is used as the inorganic material layer 16, the thickness of the tantalum oxide layer is, for example, 200 nm.

The thickness of the inorganic material layer 16 is preferably not less than 100 nm and less than 500 nm. If the thickness of the inorganic material layer 16 is less than 100 nm, there is a probability that a defect (typically, a void; i.e., a gap between crystal grains) occurs in the aluminum film 18. If the thickness of the inorganic material layer 16 is not less than 500 nm, insulation is likely to occur between the aluminum base 12 and the aluminum film 18 due to the surface condition of the aluminum base 12. To realize anodization of the aluminum film 18 by supplying an electric current from the aluminum base 12 side to the aluminum film 18, the electric current needs to flow between the aluminum base 12 and the aluminum film 18. When employing a configuration where an electric current is supplied from the inside surface of the aluminum base 12 in the shape of a hollow cylinder, it is not necessary to provide an electrode to the aluminum film 18. Therefore, the aluminum film 18 can be anodized across the entire surface, while such a problem does not occur that supply of the electric current becomes more difficult as the anodization advances. Thus, the aluminum film 18 can be anodized uniformly across the entire surface.

To form a thick inorganic material layer 16, it is in general necessary to increase the film formation duration. When the film formation duration is increased, the surface temperature of the aluminum base 12 unnecessarily increases, and as a result, the film quality of the aluminum film 18 deteriorates, and a defect (typically, a void) occurs in some cases. When the thickness of the inorganic material layer 16 is less than 500 nm, occurrence of such a problem can be suppressed.

The aluminum film 18 is, for example, a film which is made of aluminum whose purity is not less than 99.99 mass % (hereinafter, sometimes referred to as "high-purity aluminum film") as disclosed in Patent Document 3. The aluminum film 18 is formed by, for example, vacuum evaporation or sputtering. The thickness of the aluminum film 18 is preferably in the range of not less than about 500 nm and not more than about 1500 nm. For example, the thickness of the aluminum film 18 is about 1 μm.

The aluminum film 18 may be an aluminum alloy film disclosed in Patent Document 4 in substitution for the high-purity aluminum film. The aluminum alloy film disclosed in Patent Document 4 contains aluminum, a metal element other than aluminum, and nitrogen. In this specification, the "aluminum film" includes not only the high-purity aluminum film but also the aluminum alloy film disclosed in Patent Document 4.

Using the above-described aluminum alloy film enables to obtain a specular surface whose reflectance is not less than 80%. The average grain diameter of crystal grains that form the aluminum alloy film when viewed in the normal direction of the aluminum alloy film is, for example, not more than 100 nm, and that the maximum surface roughness Rmax of the aluminum alloy film is not more than 60 nm. The content of nitrogen in the aluminum alloy film is, for example, not less than 0.5 mass % and not more than 5.7 mass %. It is preferred that the absolute value of the difference between the standard electrode potential of the metal element other than aluminum which is contained in the aluminum alloy film and the standard electrode potential of aluminum is not more than 0.64 V, and that the content of the metal element in the aluminum alloy film is not less than 1.0 mass % and not more than 1.9 mass %. The metal element is, for example, Ti or Nd. The metal element is not limited to these examples but may be such a different metal element that the absolute value of the difference between the standard electrode potential of the metal element and the standard electrode potential of aluminum is not more than 0.64 V (for example, Mn, Mg, Zr, V, and Pb). Further, the metal element may be Mo, Nb, or Hf. The aluminum alloy film may contain two or more of these metal elements. The aluminum alloy film is formed by, for example, a DC magnetron sputtering method. The thickness of the aluminum alloy film is also preferably in the range of not less than about 500 nm and not more than about 1500 nm. For example, the thickness of the aluminum alloy film is about 1 μm.

Then, a surface 18s of the aluminum film 18 is anodized to form a porous alumina layer 14 which has a plurality of recessed portions (micropores) 14p as shown in FIG. 2(b). The porous alumina layer 14 includes a porous layer which has the recessed portions 14p and a barrier layer (the base of the recessed portions (micropores) 14p). As known in the art, the interval between adjacent recessed portions 14p (the distance between the centers) is approximately twice the thickness of the barrier layer and is approximately proportional to the voltage that is applied during the anodization. This relationship also applies to the final porous alumina layer 14 shown in FIG. 2(e).

The porous alumina layer 14 is formed by, for example, anodizing the surface 18s in an acidic electrolytic solution. The electrolytic solution used in the step of forming the porous alumina layer 14 is, for example, an aqueous solution which contains an acid selected from the group consisting of oxalic acid, tartaric acid, phosphoric acid, sulfuric acid, chromic acid, citric acid, and malic acid. For example, the surface 18s of the aluminum film 18 is anodized with an applied voltage of 80 V for 55 seconds using an oxalic acid aqueous solution (concentration: 0.3 mass %, solution temperature: 10° C.), whereby the porous alumina layer 14 is formed.

Then, the porous alumina layer 14 is brought into contact with an alumina etchant such that a predetermined amount is etched away, whereby the opening of the recessed portions 14p is enlarged as shown in FIG. 2(c). By modifying the type and concentration of the etching solution and the etching duration, the etching amount (i.e., the size and depth of the recessed portions 14p) can be controlled. The etching solution used may be, for example, an aqueous solution of 10 mass % phosphoric acid, organic acid such as formic acid, acetic acid or citric acid, or sulfuric acid, or a chromate-phosphate mixture aqueous solution. For example, the etching is performed for 20 minutes using a phosphoric acid aqueous solution (10 mass %, 30° C.)

Then, the aluminum film 18 is again partially anodized such that the recessed portions 14p are grown in the depth direction and the thickness of the porous alumina layer 14 is increased as shown in FIG. 2(d). Here, the growth of the recessed portions 14p starts at the bottoms of the previously-formed recessed portions 14p, and accordingly, the lateral surfaces of the recessed portions 14p have stepped shapes.

Thereafter, when necessary, the porous alumina layer 14 may be brought into contact with an alumina etchant to be further etched such that the pore diameter of the recessed portions 14p is further increased. The etching solution used in this step may preferably be the above-described etching solution. Practically, the same etching bath may be used.

In this way, by alternately repeating the anodization step and the etching step as described above through multiple cycles (e.g., 5 cycles: including 5 anodization cycles and 4 etching cycles), the moth-eye mold 100A that includes the porous alumina layer 14 which has the inverted moth-eye structure is obtained as shown in FIG. 2(e). Since the process is ended with the anodization step, the recessed portions 14p have pointed bottom portion. That is, the resultant mold enables formation of raised portions with pointed tip ends.

The porous alumina layer 14 (thickness: $t_p$) shown in FIG. 2(e) includes a porous layer (whose thickness is equivalent to the depth $D_d$ of the recessed portions 14p) and a barrier layer (thickness: $t_b$). Since the porous alumina layer 14 has a structure obtained by inverting the moth-eye structure of the synthetic polymer film 34A, corresponding parameters which define the dimensions may sometimes be designated by the same symbols.

The recessed portions 14p of the porous alumina layer 14 may have, for example, a conical shape and may have a stepped lateral surface. It is preferred that the two-dimensional size of the recessed portions 14p (the diameter of a circle equivalent to the area of the recessed portions 14p when viewed in a normal direction of the surface), $D_p$, is more than 20 nm and less than 500 nm, and the depth of the recessed portions 14p, $D_d$, is not less than 50 nm and less than 1000 nm (1 μm). It is also preferred that the bottom portion of the recessed portions 14p is acute (with the deepest part of the bottom portion being pointed). When the recessed portions 14p are in a densely packed arrangement, assuming that the shape of the recessed portions 14p when viewed in a normal direction of the porous alumina layer 14 is a circle, adjacent circles overlap each other, and a saddle portion is formed between adjacent ones of the recessed portions 14p. Note that, when the generally-conical recessed portions 14p adjoin one another so as to form saddle portions, the two-dimensional size of the recessed portions 14p, $D_p$, is equal to the adjoining distance $D_{int}$. The thickness of the porous alumina layer 14, $t_p$, is not more than about 1 μm.

Under the porous alumina layer 14 shown in FIG. 2(e), there is an aluminum remnant layer 18r. The aluminum remnant layer 18r is part of the aluminum film 18 which has not been anodized. When necessary, the aluminum film 18 may be substantially thoroughly anodized such that the aluminum remnant layer 18r is not present. For example, when the inorganic material layer 16 has a small thickness, it is possible to readily supply an electric current from the aluminum base 12 side.

The manufacturing method of the moth-eye mold illustrated herein enables manufacture of a mold which is for production of antireflection films disclosed in Patent Documents 2 to 4. Since an antireflection film used in a high-definition display panel is required to have high uniformity, selection of the material of the aluminum base, specular working of the aluminum base, and control of the purity and components of the aluminum film are preferably carried out as described above. However, the above-described mold manufacturing method can be simplified because the microbicidal activity can be achieved without high uniformity. For example, the surface of the aluminum base may be directly anodized. Even if, in this case, pits are formed due to impurities contained in the aluminum base, only local structural irregularities occur in the moth-eye structure of the finally-obtained synthetic polymer film 34A, and it is estimated that there is little adverse influence on the microbicidal activity.

According to the above-described mold manufacturing method, a mold in which the regularity of the arrangement of the recessed portions is low, and which is suitable to production of an antireflection film, can be manufactured. In the case of utilizing the microbicidal ability of the moth-eye structure, it is estimated that the regularity of the arrangement of the raised portions does not exert an influence. A mold for formation of a moth-eye structure which has regularly-arranged raised portions can be manufactured, for example, as described in the following section.

For example, after formation of a porous alumina layer having a thickness of about 10 μm, the formed porous alumina layer is removed by etching, and then, anodization may be performed under the conditions for formation of the above-described porous alumina layer. A 10 μm thick porous alumina layer is realized by extending the anodization duration. When such a relatively thick porous alumina layer is formed and then this porous alumina layer is removed, a porous alumina layer having regularly-arranged recessed portions can be formed without being influenced by irregularities which are attributed to grains that are present at the surface of an aluminum film or aluminum base or the process strain. Note that, in removal of the porous alumina layer, using a mixture solution of a chromate and a phosphate is preferred. Although continuing the etching for a long period of time sometimes causes galvanic corrosion, the mixture solution of a chromate and a phosphate has the effect of suppressing galvanic corrosion.

A moth-eye mold for production of the synthetic polymer film 34B shown in FIG. 1(b) can be, basically, manufactured by combination of the above-described anodization step and etching step. A manufacturing method of a moth-eye mold 100B that is for production of the synthetic polymer film 34B is described with reference to FIGS. 3(a) to 3(c).

Firstly, in the same way as illustrated with reference to FIGS. 2(a) and 2(b), the mold base 10 is provided, and the surface 18s of the aluminum film 18 is anodized, whereby a porous alumina layer 14 which has a plurality of recessed portions (micropores) 14p is formed.

Figure 2:
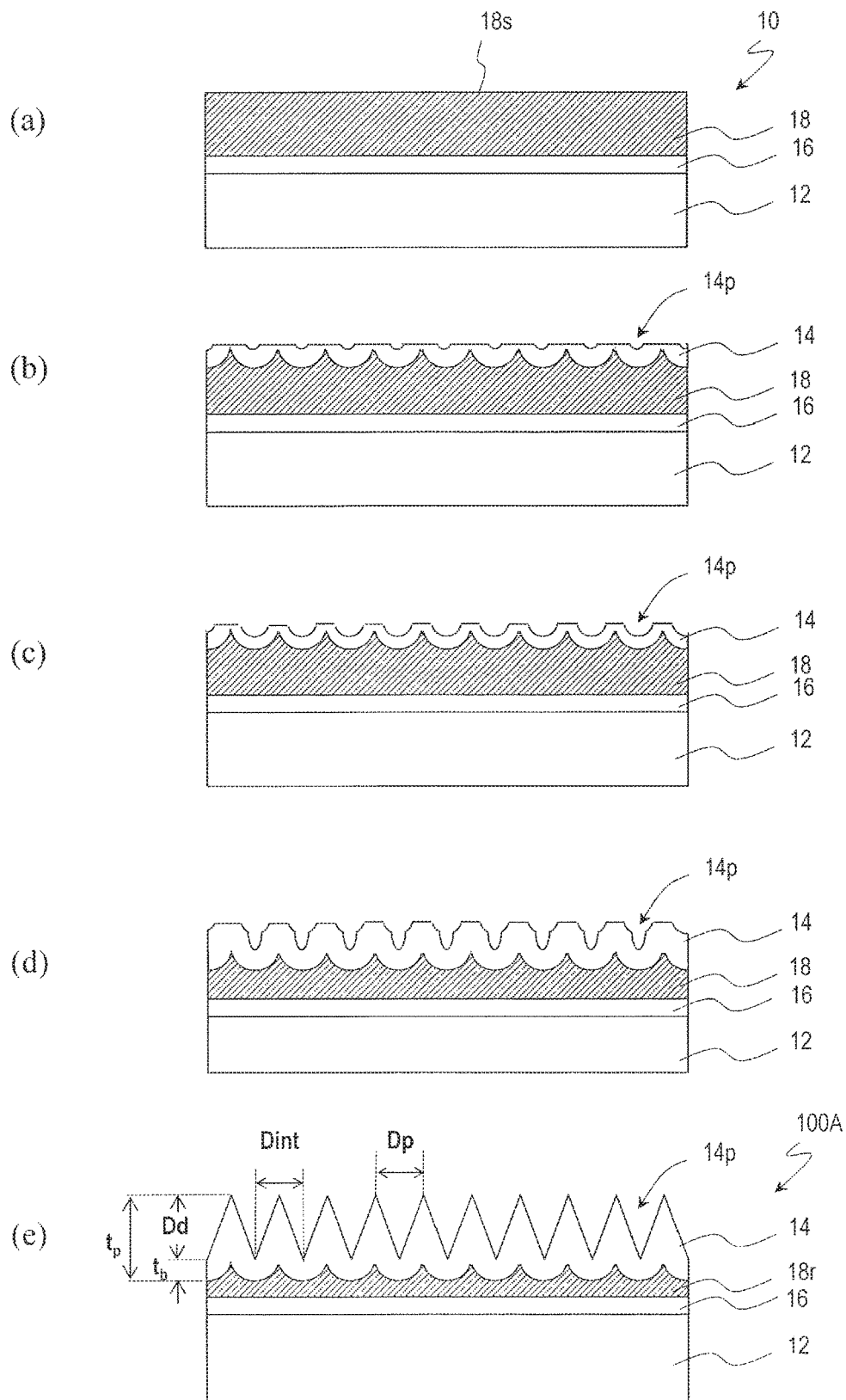
FIG. 2 (a) to (e) are diagrams for illustrating a method for manufacturing a moth-eye mold 100A and a configuration of the moth-eye mold 100A.
Figure 3:
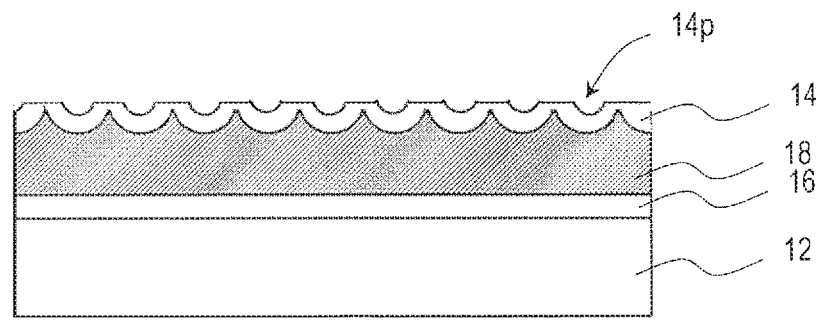
FIG. 3 (a) to (c) are diagrams for illustrating a method for manufacturing a moth-eye mold 100B and a configuration of the moth-eye mold 100B.
Figure 3:
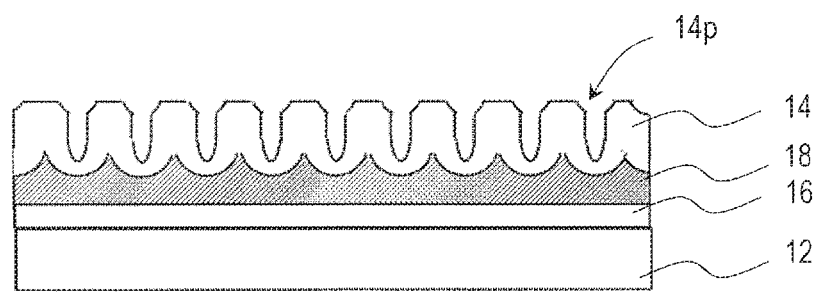
Figure 3:
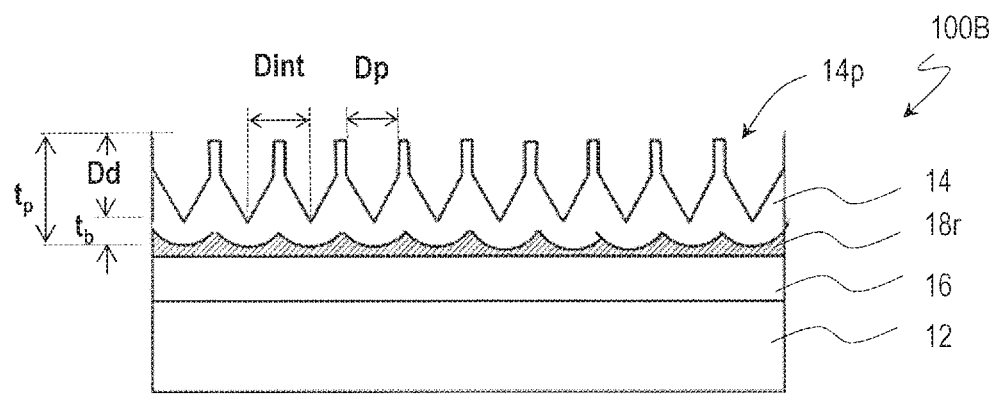

Then, the porous alumina layer 14 is brought into contact with an alumina etchant such that a predetermined amount is etched away, whereby the opening of the recessed portions 14p is enlarged as shown in FIG. 3(a). In this step, the etched amount is smaller than in the etching step illustrated with reference to FIG. 2(c). That is, the size of the opening of the recessed portions 14p is decreased. For example, the etching is performed for 10 minutes using a phosphoric acid aqueous solution (10 mass %, 30° C.).

Then, the aluminum film 18 is again partially anodized such that the recessed portions 14p are grown in the depth direction and the thickness of the porous alumina layer 14 is increased as shown in FIG. 3(b). In this step, the recessed portions 14p are grown deeper than in the anodization step illustrated with reference to FIG. 2(d). For example, the anodization is carried out with an applied voltage of 80 V for 165 seconds (in FIG. 2(d), 55 seconds) using an oxalic acid aqueous solution (concentration: 0.3 mass %, solution temperature: 10° C.).

Thereafter, the etching step and the anodization step are alternately repeated through multiple cycles in the same way as illustrated with reference to FIG. 2(e). For example, 3 cycles of the etching step and 3 cycles of the anodization step are alternately repeated, whereby the moth-eye mold 100B including the porous alumina layer 14 which has the inverted moth-eye structure is obtained as shown in FIG. 3(c). In this step, the two-dimensional size of the recessed portions 14p, $D_p$, is smaller than the adjoining distance $D_{int}$ ($D_p < D_{int}$).

Figure 4:
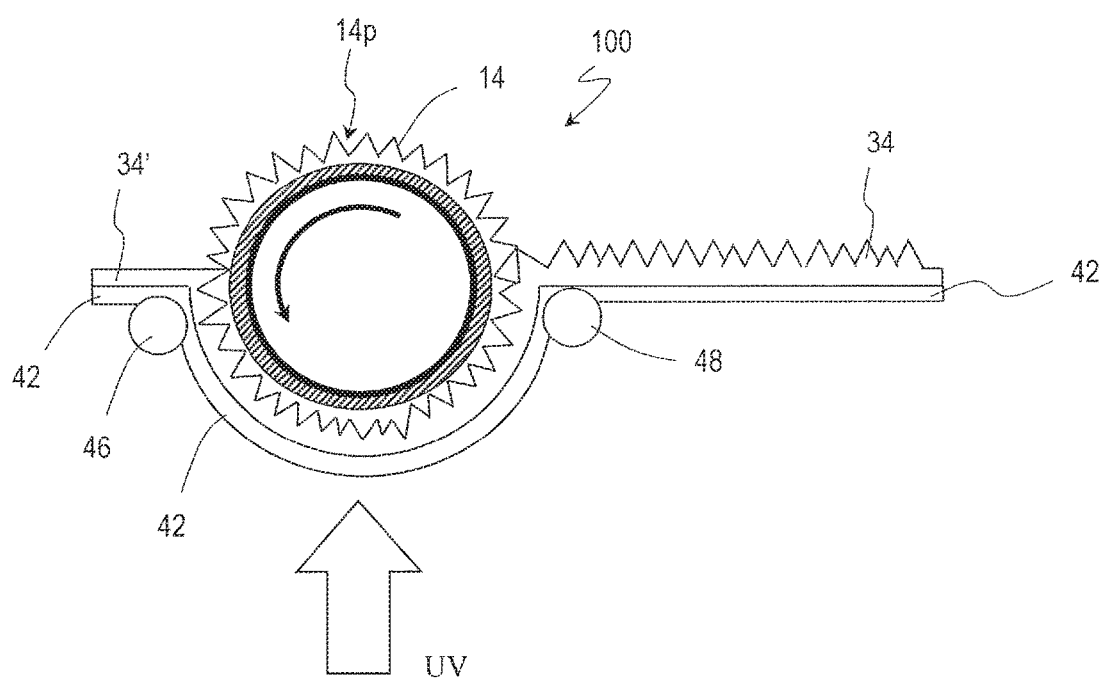
FIG. 4 A diagram for illustrating a method for producing a synthetic polymer film with the use of the moth-eye mold 100.

Next, a method for producing a synthetic polymer film with the use of a moth-eye mold 100 is described with reference to FIG. 4. FIG. 4 is a schematic cross-sectional view for illustrating a method for producing a synthetic polymer film according to a roll-to-roll method.

First, a moth-eye mold 100 in the shape of a hollow cylinder is provided. Note that the moth-eye mold 100 in the shape of a hollow cylinder is manufactured according to, for example, the manufacturing method described with reference to FIG. 2.

As shown in FIG. 4, a base film 42 over which a UV-curable resin 34' is applied on its surface is maintained pressed against the moth-eye mold 100, and the UV-curable resin 34' is irradiated with ultraviolet (UV) light such that the UV-curable resin 34' is cured. The UV-curable resin 34' used may be, for example, an acrylic resin. The base film 42 may be, for example, a PET (polyethylene terephthalate) film or TAC (triacetyl cellulose) film. The base film 42 is fed from an unshown feeder roller, and thereafter, the UV-curable resin 34' is applied over the surface of the base film 42 using, for example, a slit coater or the like. The base film 42 is supported by supporting rollers 46 and 48 as shown in FIG. 4. The supporting rollers 46 and 48 have rotation mechanisms for carrying the base film 42. The moth-eye mold 100 in the shape of a hollow cylinder is rotated at a rotation speed corresponding to the carrying speed of the base film 42 in a direction indicated by the arrow in FIG. 4.

Thereafter, the moth-eye mold 100 is separated from the base film 42, whereby a synthetic polymer film 34 to which the inverted moth-eye structure of the moth-eye mold 100 is transferred is formed on the surface of the base film 42. The base film 42 which has the synthetic polymer film 34 formed on the surface is wound up by an unshown winding roller.

The surface of the synthetic polymer film 34 has the moth-eye structure obtained by inverting the surficial nanostructures of the moth-eye mold 100. According to the surficial nanostructure of the moth-eye mold 100 used, the synthetic polymer films 34A and 34B shown in FIGS. 1(a) and 1(b), respectively, can be produced. The material that forms the synthetic polymer film 34 is not limited to the UV-curable resin but may be a photocurable resin which is curable by visible light or may be a thermosetting resin.

Hereinafter, it is explained with experimental examples that the synthetic polymer film which has the above-described moth-eye structure over its surface has the microbicidal ability.

A mold manufactured according to the above-described mold manufacturing method was used to produce a synthetic polymer film having conical raised portions such as the raised portions 34Ap of the film 50A shown in FIG. 1(a). In sample films subjected to evaluation of the microbicidal activity, $D_p$ was about 200 nm, $D_{int}$ was about 200 nm, and $D_h$ was about 150 nm (see FIG. 5, for example). From the viewpoint of causing local deformation of the cell wall, it is preferred that there is a large distance between adjoining raised portions. The difference between $D_p$ and $D_{int}$ is preferably, for example, 0 times to twice $D_p$, and more preferably 0.5 times to twice $D_p$. Here, $D_p$, $D_{int}$, and $D_h$ represent the average values determined from SEM images.

In photographing of the SEM images, a field emission scanning electron microscope (S-4700 manufactured by Hitachi, Ltd.) was used.

As the resin material that forms the synthetic polymer film, a UV-curable resin was used. Sample films No. 1 to No. 3 were produced using acrylic resins which include the nitrogen element in different proportions. The atomic concentration in each sample film was measured by XPS (X-ray Photoelectron Spectroscopy).

Sample film No. 1 was produced using acrylic resin A which did not include a nitrogen element. Acrylic resin A did not include urethane acrylate. The number of functional groups included in acrylic resin A was 3.43 (tetramethylolmethane triacrylate: 57 mol %, tetramethylolmethane tetraacrylate: 43 mol %).

Sample film No. 2 was produced using acrylic resin B which included urethane acrylate. In urethane acrylate-containing acrylic resin B, the atomic concentration of the nitrogen element was 0.7 at %. In urethane acrylate-containing acrylic resin B, the content of a resin which included 3 functional groups was 31.8 mass %, the content of acrylic resin A which included 3.43 functional groups was 28.2 mass %, and the content of a resin which included 4 functional groups was 40.0 mass %.

Sample film No. 3 was produced using acrylic resin C which included urethane acrylate. In urethane acrylate-containing acrylic resin C, the atomic concentration of the nitrogen element was 2.2 at %. The number of functional groups included in urethane acrylate-containing acrylic resin C was 3.

In experiment 1 to experiment 3 described below, the relationship between the concentration of the nitrogen element included in the synthetic polymer film and the microbicidal effect of the synthetic polymer film is mainly discussed.

EXPERIMENT 1

Sample films No. 1 and No. 2 were first evaluated as to the microbicidal ability. The evaluation of the microbicidal ability was carried out through the following procedure:

1. Beads with frozen *P. aeruginosa* bacteria (purchased from National Institute of Technology and Evaluation) were immersed in a broth at 37° C. for 24 hours, whereby the *P. aeruginosa* bacteria were thawed;
2. Centrifugation (3000 rpm, 10 minutes);
3. The supernatant of the broth was removed;
4. Sterilized water was added, and the resultant solution was stirred and thereafter subjected to centrifugation again;
5. Steps 2 to 4 were repeated three times to obtain an undiluted bacterial solution (the bacteria count was of the order of 1E+07 CFU/mL);
6. 1/500 NB culture medium and bacterial dilution A (the bacteria count was of the order of 1E+05 CFU/mL) were prepared.

1/500 NB culture medium: NB culture medium (nutrient broth medium E-MC35 manufactured by Eiken Chemical Co., Ltd.) was diluted 500-fold with sterilized water.

Bacterial Dilution A: Undiluted Bacterial Solution 500 µL+Sterilized Water 49.5 mL;

7. Bacterial dilution B was prepared by adding the 1/500 NB culture medium as a nutrient source to bacterial dilution A (in accordance with JIS Z2801 5.4a))
8. A 400 µL drop of bacterial dilution B (the bacteria count in the bacterial dilution B at this point in time is also referred to as "initial bacteria count") was placed on each of the sample films. A cover (e.g., cover glass) was placed over the bacterial dilution B to adjust the amount of the bacterial dilution B per unit area.
9. The samples were left in an environment where the temperature was 37° C. and the relative humidity was 100% for a predetermined time period (time period: 5 minutes, 4 hours, 24 hours, or 48 hours).
10. The entire sample film with the bacterial dilution B and 9.6 mL sterilized water were put into a filter bag. The sample film was rubbed with hands over the filter bag to sufficiently wash away the bacteria from the sample film. The post-wash solution in the filter bag was a 25-fold dilution of the bacterial dilution B. This post-wash solution is also referred to as "bacterial dilution B2". The bacteria count of the bacterial dilution B2 is to be of the order of 1E+04 CFU/mL if the bacteria count in the bacterial dilution B does not increase or decrease.
11. The bacterial dilution B2 was diluted 10-fold, whereby bacterial dilution C was prepared. Specifically, the bacterial dilution C was prepared by putting 120 µL of the post-wash solution (bacterial dilution B2) into 1.08 mL sterilized water. The bacteria count of the bacterial dilution C is to be of the order of 1E+03 CFU/mL if the bacteria count in the bacterial dilution B does not increase or decrease.
12. The bacterial dilution C was diluted 10-fold in the same way as that for preparation of the bacterial dilution C, whereby bacterial dilution D was prepared. The bacteria count of the bacterial dilution D is to be of the order of 1E+02 CFU/mL if the bacteria count in the bacterial dilution B does not increase or decrease. Further the bacterial dilution D was diluted 10-fold, whereby bacterial dilution E was prepared. The bacteria count of the bacterial dilution E is to be of the order of 1E+01 CFU/mL if the bacteria count in the bacterial dilution B does not increase or decrease.
13. 1 mL drops of the bacterial dilution B2 and the bacterial dilutions C to E were placed on Petrifilm™ media (product name: Aerobic Count Plate (AC), manufactured by 3M). The bacteria were cultured at 37° C. with the relative humidity of 100%. After 48 hours, the number of bacteria in the bacterial dilution B2 was counted.

Note that, although in JIS Z2801 5.6h) a phosphate-buffered saline is used in preparation of a diluted solution, sterilized water was used in experiment 1. When sterilized water is used, there is a probability that the difference in osmotic pressure from the solution in the cells of microorganism, rather than the physical structure and chemical properties of the surface of the sample films, will be a cause of death of bacteria. As for this probability, it was verified that bacteria would not die on sample film No. 5 (PET) which will be described later. It was verified that the microbicidal effect which is attributed to the physical structure and chemical properties of the surface of the sample films can be examined even when sterilized water is used.

Evaluation of the microbicidal ability was carried out with sample film No. 1 having the initial bacteria count of 3.1E+05 CFU/mL and sample film No. 2 having the initial bacteria count of 1.4E+05 CFU/mL. Sample film No. 1 was not measured for a case where the time period for which the sample film was left was 5 minutes.

Figure 5:
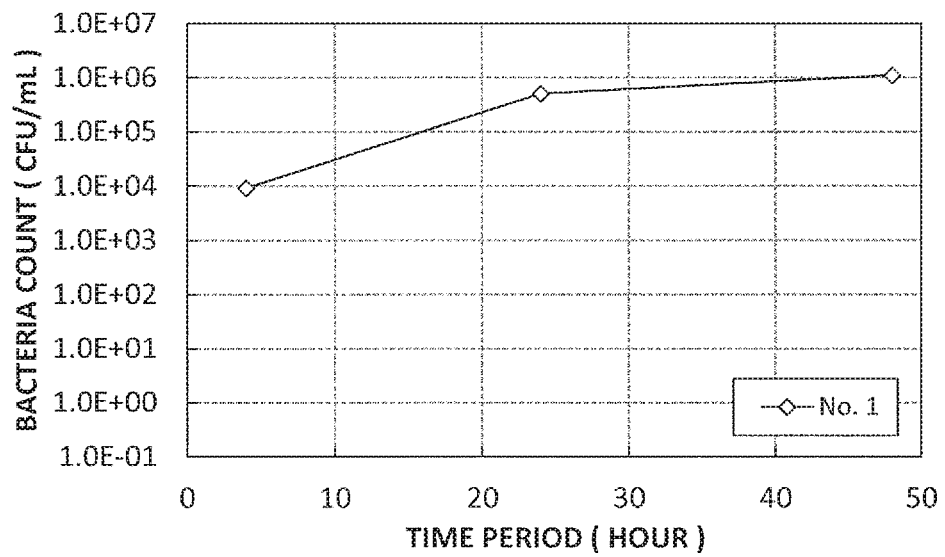
FIG. 5 (a) is a graph showing the results of evaluation of the microbicidal ability of sample film No. 1 in experiment 1. (b) is a graph showing the results of evaluation of the microbicidal ability of sample film No. 2 in experiment 1. In (a) and (b), the horizontal axis represents the time period for which the sample was left (hour), and the vertical axis represents the bacteria count in bacterial dilution B2 (CFU/mL).
Figure 5:
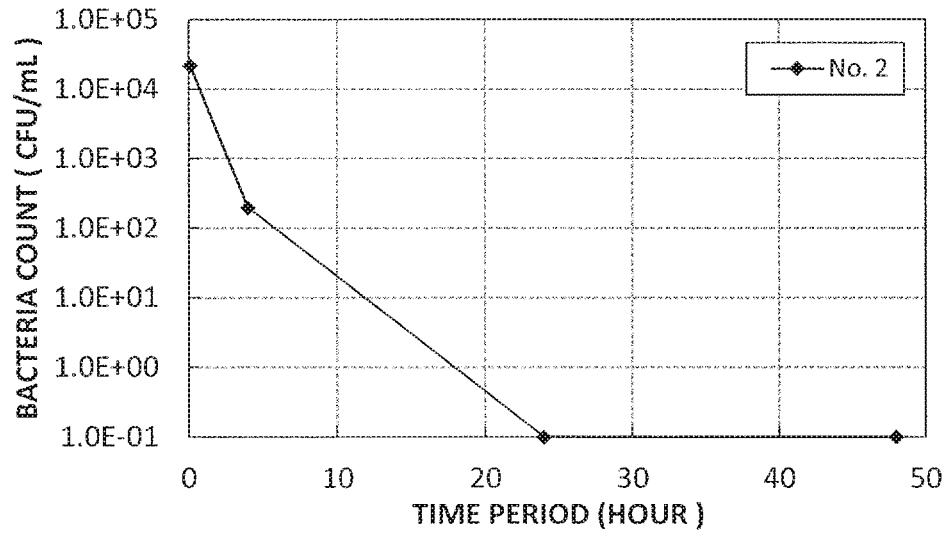

The results are shown in FIG. 5. FIG. 5(*a*) is a graph showing the results of evaluation of the microbicidal ability of sample film No. 1 in experiment 1. FIG. 5(*b*) is a graph showing the results of evaluation of the microbicidal ability of sample film No. 2 in experiment 1. In FIG. 5, the horizontal axis represents the time period for which the sample film was left (hour), and the vertical axis represents the bacteria count in bacterial dilution B2 (CFU/mL). Note that, in FIG. 5, when the bacteria count is 0, it is plotted as 0.1 for the sake of visibility.

As seen from FIGS. 5(a) and 5(b), sample film No. 2 which was made of a resin which included the nitrogen element exhibited a microbicidal ability, while sample film No. 1 which was made of a resin which did not include the nitrogen element did not exhibit a microbicidal ability.

As seen from the experimental results, when a synthetic polymer film includes a nitrogen element, the synthetic polymer film has a microbicidal ability. It was found that the synthetic polymer film preferably includes the nitrogen element in a proportion of, for example, not less than 0.7 at %.

EXPERIMENT 2

Next, sample films No. 2 and No. 3 were evaluated as to the microbicidal ability with changed values for the initial bacteria count. In experiment 2, the initial bacteria count was of the order of 1E+06 CFU/mL while it was of the order of 1E+05 CFU/mL in experiment 1. The procedure of evaluation was basically the same as that of experiment 1. Note that, however, the time period for which the sample films were left in an environment where the temperature was 37° C. and the relative humidity was 100% was 67.5 hours.

It was found from the experimental results that sample film No. 3 had a microbicidal ability while a sufficient microbicidal effect was not achieved in sample film No. 2. It is inferred that a sufficient microbicidal effect was not achieved in experiment 2 because of the increased initial bacteria count, although it was found in experiment 1 that sample film No. 2 had a microbicidal ability. The relationship between the initial bacteria count and the microbicidal effect will be described later.

It can be seen from the results of experiment 2 that a synthetic polymer film has a greater microbicidal ability as the atomic concentration of the nitrogen element included in the synthetic polymer film increases. It was found that, more preferably, the synthetic polymer film includes the nitrogen element in a proportion of not less than 2.2 at %.

EXPERIMENT 3

Next, sample films No. 1 to No. 5 were evaluated as to the microbicidal ability under the conditions that the initial bacteria count was 2.5E+06 CFU/mL and the nutrient source in the bacterial dilution B was 10 times that of experiment 1. Specifically, 1/50 NB culture medium (prepared by diluting a NB culture medium (nutrient broth medium E-MC35 manufactured by Eiken Chemical Co., Ltd.) 50-fold with sterilized water) was added as the nutrient source to the bacterial dilution A, whereby bacterial dilution B was prepared.

Sample film No. 4 was produced using the same urethane acrylate-containing acrylic resin B as that used for sample film No. 2. Sample film No. 4 was different from sample film No. 2 in that sample film No. 4 did not have a moth-eye structure over the surface.

Sample film No. 5 was a PET film which was the same as that used as the base film of sample films No. 1 to No. 4.

The procedure of evaluation was basically the same as that of experiment 1.

Figure 6:
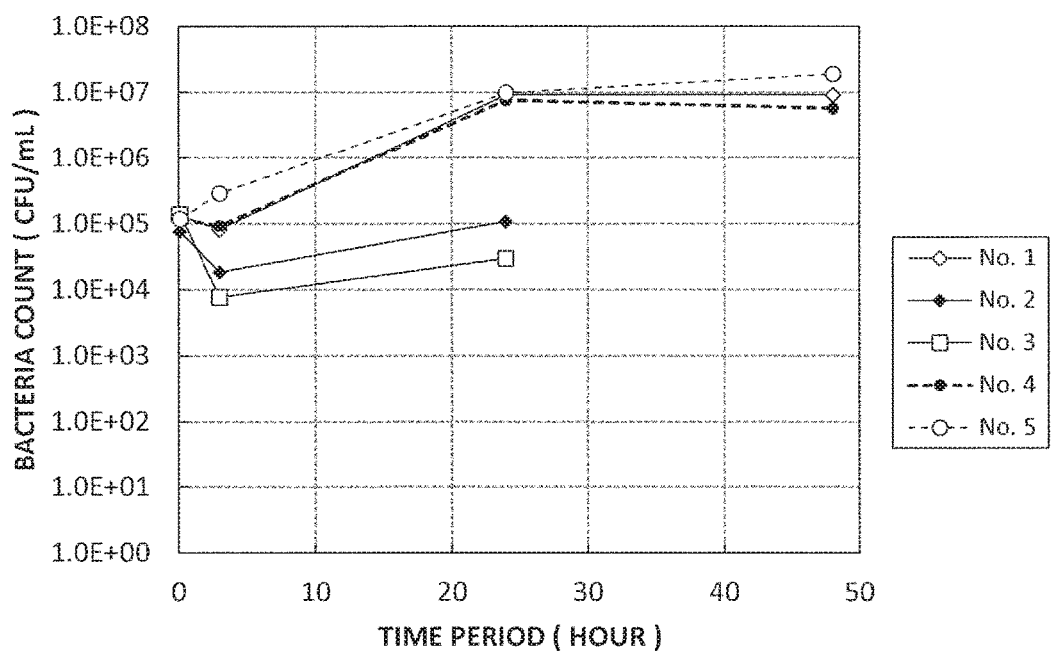
FIG. 6 Graph showing the results of evaluation of the microbicidal ability of sample films No. 1 to No. 5 in experiment 3. The horizontal axis represents the time period for which the samples were left (hour), and the vertical axis represents the bacteria count in bacterial dilution B2 (CFU/mL).

The results are shown in FIG. 6. FIG. 6 is a graph showing the results of evaluation of the microbicidal ability of sample films No. 1 to No. 5 in experiment 3. In FIG. 6, the horizontal axis represents the time period for which the sample films were left (hour), and the vertical axis represents the bacteria count in bacterial dilution B2 (CFU/mL).

As seen from FIG. 6, in sample films No. 2 and No. 3, the bacteria count did not decrease when the time period for which the sample films were left changed from 3 hours to 24 hours, but increase of the bacteria count was suppressed as compared with sample film No. 5 in which increase of the bacteria count was largest. That is, it was verified that sample films No. 2 and No. 3 which included the nitrogen element had an antimicrobial effect (microbiostatic effect) which is capable of suppressing increase of the bacteria count. Sample film No. 3 which was made of a resin in which the atomic concentration of the nitrogen element was higher (2.2 at %) exhibited a better antimicrobial effect than sample film No. 2 (0.7 at %).

It can also be seen from comparison of the results of sample films No. 2 and No. 4 that sample film No. 2 which has a moth-eye structure over the surface has a better antimicrobial effect than sample film No. 4. It can be seen that, since the synthetic polymer film has a moth-eye structure over the surface and the nitrogen element is included in the synthetic polymer film, the synthetic polymer film has an excellent microbicidal effect and/or antimicrobial effect.

The present inventors examined the relationship between the initial bacteria count and the microbicidal effect as described below.

Growth of bacteria proceeds in such a manner that one bacterium divides into two every generation time $T_0$ so that the number of bacteria doubles. That is, as represented by formula (1) below, the number of bacteria at time $t=nT_0$, $N(nT_0)$, is twice the number of bacteria at time $t=(n-1)T_0$, $N((n-1)T_0)$. Here, n is a positive integer.

[Equation 1]

$$N(nT_0)=2N((n-1)T_0) \tag{1}$$

Generation time $T_0$ varies depending on the type of the bacterium and the culture conditions. For example, the generation time of *P. aeruginosa* under conditions suitable to growth is about 30 minutes to 40 minutes. Formula (1) can be expressed as formula (2) using the number of bacteria at time $t=0$, $N(0)$.

[Equation 2]

$$N(nT_0)=2^n\{N(0)\} \tag{2}$$

From formula (2), the number of bacteria at time t, $N(t)$, can be expressed as formula (3). The number of bacteria logarithmically increases with time.

[Equation 3]

$$N(t)=2^{t/T_0}\{N(0)\} \tag{3}$$

The number of bacteria on a synthetic polymer film which has a microbicidal effect is examined based on the above-described concept of growth. Where D is the number of bacteria killed at the surface of the synthetic polymer film (sample film) per unit time, the number of bacteria at time $t=nT_0$, $N(nT_0)$, can be expressed as formula (4) shown below.

[Equation 4]

$$N(nT_0)=2N((n-1)T_0)-DT_0 \tag{4}$$

Formula (4) is obtained by adding a term which represents the microbicidal effect ($-DT_0$) to formula (1) shown above. Formula (4) can be modified into formula (5).

[Equation 5]

$$N(nT_0)=DT_0+2^n\{N(0)-DT_0\} \tag{5}$$

From formula (5), the number of bacteria at time t, N(t), can be expressed as formula (6).

[Equation 6]

$$N(t) = DT_0 + 2^{t/T_0}\{N(0) - DT_0\} \qquad (6)$$

According to formula (6), the number of bacteria at time t, N(t), is determined depending on which of the number of bacteria at time t=0 (i.e., initial bacteria count), N(0), and the number of bacteria killed per generation time, $DT_0$, is greater than the other. If the initial bacteria count N(0) is greater than the number of bacteria killed per generation time $DT_0$ (N(0)>$DT_0$), the number of bacteria continues to increase with time t. If the initial bacteria count N(0) is smaller than the number of bacteria killed per generation time $DT_0$ (N(0)<$DT_0$), the number of bacteria decreases with time t. After the passage of a finite time period, the number of bacteria becomes 0.

As described above, the microbicidal effect of sample film No. 2 was verified in experiment 1, while in experiment 2 in which the initial bacteria count was increased, the microbicidal effect of sample film No. 2 was not sufficiently achieved. These results can be explained according to formula (6). It is considered that the initial bacteria count in experiment 1 was smaller than the number of bacteria per generation time sample film No. 2 can kill, while the initial bacteria count in experiment 2 was greater than the number of bacteria per generation time sample film No. 2 can kill.

Note that formula (6) is a simplified model, and therefore, factors which are not reflected in formula (6) need to be considered in some cases. For example, although in formula (6) the number of bacteria killed per unit time, D, is constant irrespective of the number of bacteria, there is a probability that it varies depending on the number of bacteria.

The influence of the amount of the nutrient source for bacteria (e.g., organic substance) on the microbicidal effect also needs to be considered in some cases. For example, in experiment 3 in which the nutrient source was increased, sample films No. 2 and No. 3 did not exhibit a sufficient microbicidal effect as compared with experiment 2 and only suppressed increase of the bacteria count. In general, according to for example the Monod equation, the growth rate increases as the nutrient source increases. That is, generation time $T_0$ is shorter as the nutrient source increases. In this case, as seen from formula (6), the initial bacteria count needs to be smaller for achieving a microbicidal effect.

Microorganisms generally have a surface structure which is capable of easily attaching to the surface of an object in order to increase the probability of being in contact with an organic substance that is the nutrient source. Therefore, if the amount of the nutrient source is small, it is probable that the attachability to the object surface is amplified. It is also probable that this enables more efficient sterilization at the surface of the synthetic polymer film.

A cell generally has the mechanism of taking a polar substance (including a nutrient source) into the cell (endocytosis). Actually, as will be described later with reference to FIG. 8, the raised portions of synthetic polymer film appear to be taken into the cell wall. When the amount of the nutrient source is small, it is also probable that the efficiency of taking the raised portions of the synthetic polymer film into the cell wall is amplified, so that bacteria are efficiently killed at the surface of the synthetic polymer film.

Note that, when bacteria are cultured, the bacteria do not necessarily logarithmically grow as described by formula (1) to formula (6) for all of the culture times. Before a logarithmic phase (logarithmic growth phase) such as described by formula (1) to formula (6), a lag phase sometimes occurs in which the number of bacteria rarely varies. The lag phase is a period where bacteria rarely divide. This period is considered to be for preparation for division (e.g., cell repairing, biosynthesis of enzymes) and adaptation to the medium. For example, according to the results of experiment 3 shown in FIG. 6, in sample films No. 1 to No. 4, the bacteria count decreased after the sample films were left for 3 hours but increased after the sample films were left for 24 hours. It is considered that such a behavior reflected the transition from the lag phase to the logarithmic phase.

In experiment 4 and experiment 5 which will be described below, a silane coupling agent was applied to the surface of a synthetic polymer film such that the chemical properties of the surface of the synthetic polymer film was modified, and the microbicidal effect of the synthetic polymer film was evaluated. Particularly, the relationship between a functional group that a compound included in the surface of the synthetic polymer film has and the microbicidal effect of the synthetic polymer film was examined.

EXPERIMENT 4

In experiment 4, seven sample films No. 10 to No. 16 shown in Table 1 below were evaluated as to the microbicidal ability.

TABLE 1

| No. | SYNTHETIC POLYMER FILM (BASE FILM: PET) | SUBSTANCE APPLIED TO SURFACE | FUNCTIONAL GROUP |
|---|---|---|---|
| 10 | ACRYLIC RESIN D WITH SILICONE-BASED LUBRICANT ADDED | NONE | — |
| 11 | ACRYLIC RESIN D WITH SILICONE-BASED LUBRICANT ADDED | SILANE COUPLING AGENT S0 | VINYL GROUP —CH=$CH_2$ |
| 12 | ACRYLIC RESIN D WITH SILICONE-BASED LUBRICANT ADDED | SILANE COUPLING AGENT S1 | AMINO GROUP —$NH_2$ |
| 13 | ACRYLIC RESIN D WITH SILICONE-BASED LUBRICANT ADDED | SILANE COUPLING AGENT S2 | AMINO GROUP —$NH_2$ |
| 14 | ACRYLIC RESIN D WITH SILICONE-BASED LUBRICANT ADDED | SILANE COUPLING AGENT S3 | UREIDO GROUP —NHC(=O)$NH_2$ |
| 15 | ACRYLIC RESIN D WITH SILICONE-BASED LUBRICANT ADDED | SILANE COUPLING AGENT S4 | MERCAPTO GROUP —SH |
| 16 | ACRYLIC RESIN D WITH SILICONE-BASED LUBRICANT ADDED | SILANE COUPLING AGENT S5 | ISOCYANATE GROUP —N=C=O |

Sample films No. 10 to No. 16 were produced using the same mold as that described above. Sample films No. 10 to No. 16 were produced using a resin which was prepared by adding a silicone-based lubricant to acrylic resin D (which was different from acrylic resin A described above). Acrylic resin D to which a silicone-based lubricant was added did not include a nitrogen element. No surface treatment agent was applied to the surface of sample film No. 10. As for sample films No. 11 to No. 16, different silane coupling agents were applied to the surfaces of resultant synthetic polymers, whereby synthetic polymer films whose surfaces had different chemical properties (i.e., silane coupling agents applied to the surfaces had different functional groups) were prepared.

To sample film No. 11, silane coupling agent S0 was applied. Silane coupling agent S0 was KBM-1003 manufactured by Shin-Etsu Chemical Co., Ltd., which is represented by chemical formula (7) shown below. Since silane coupling agent S0 was applied to the surface, the surface of the synthetic polymer film of sample film No. 11 did not include a nitrogen element. Silane coupling agent S0 included a vinyl group (—CH=CH$_2$).

$$(CH_3O)_3SiCH=CH_2 \quad (7)$$

To sample film No. 12, silane coupling agent S1 was applied. Silane coupling agent S1 was KBM-603 manufactured by Shin-Etsu Chemical Co., Ltd., which is represented by chemical formula (8) shown below. Since silane coupling agent S1 was applied to the surface, the concentration of the nitrogen element included in the surface of the synthetic polymer film of sample film No. 12 was 5.6 at %. Silane coupling agent S1 included an amino group (—NH$_2$).

$$(CH_3O)_3SiC_3H_6NHC_2H_4NH_2 \quad (8)$$

To sample film No. 13, silane coupling agent S2 was applied. Silane coupling agent S2 was KBM-903 manufactured by Shin-Etsu Chemical Co., Ltd., which is represented by chemical formula (9) shown below. Since silane coupling agent S2 was applied to the surface, the concentration of the nitrogen element included in the surface of the synthetic polymer film of sample film No. 13 was 3.6 at %. Silane coupling agent S2 included an amino group (—NH$_2$).

$$(CH_3O)_3SiC_3H_6NH_2 \quad (9)$$

To sample film No. 14, silane coupling agent S3 was applied. Silane coupling agent S3 was KBE-585 manufactured by Shin-Etsu Chemical Co., Ltd., which is an alcohol solution of chemical formula (10) shown below. In chemical formula (10), R represents a hydrocarbon group. Silane coupling agent S3 included a ureido group (—NHC(=O) NH$_2$). The ureido group is a functional group which includes an amino group (—NH$_2$).

$$(RO)_3SiC_3H_6NHC(=O)NH_2 \quad (10)$$

To sample film No. 15, silane coupling agent S4 was applied. Silane coupling agent S4 was KBM-803 manufactured by Shin-Etsu Chemical Co., Ltd., which is represented by chemical formula (11) shown below. Since silane coupling agent S4 was applied to the surface, the concentration of the sulfur element included in the surface of the synthetic polymer film of sample film No. 15 was 3.7 at %. Silane coupling agent S4 included a mercapto group (—SH).

$$(CH_3O)_3SiC_3H_6SH \quad (11)$$

To sample film No. 16, silane coupling agent S5 was applied. Silane coupling agent S5 was KBE-9007 manufactured by Shin-Etsu Chemical Co., Ltd., which is represented by chemical formula (12) shown below. Since silane coupling agent S5 was applied to the surface, the concentration of the nitrogen element included in the surface of the synthetic polymer film of sample film No. 16 was 2.7 at %. Silane coupling agent S5 included an isocyanate group (—N=C=O).

$$(C_2H_5O)_3SiC_3H_6N=C=O \quad (12)$$

The procedure of evaluation of the microbicidal ability was basically the same as that of experiment 1 as described above. In experiment 4, the initial bacteria count for sample film No. 10 was 1.4E+05 CFU/mL, and the initial bacteria count for sample films No. 11 to No. 16 was 3.0E+05 CFU/mL.

Figure 7:
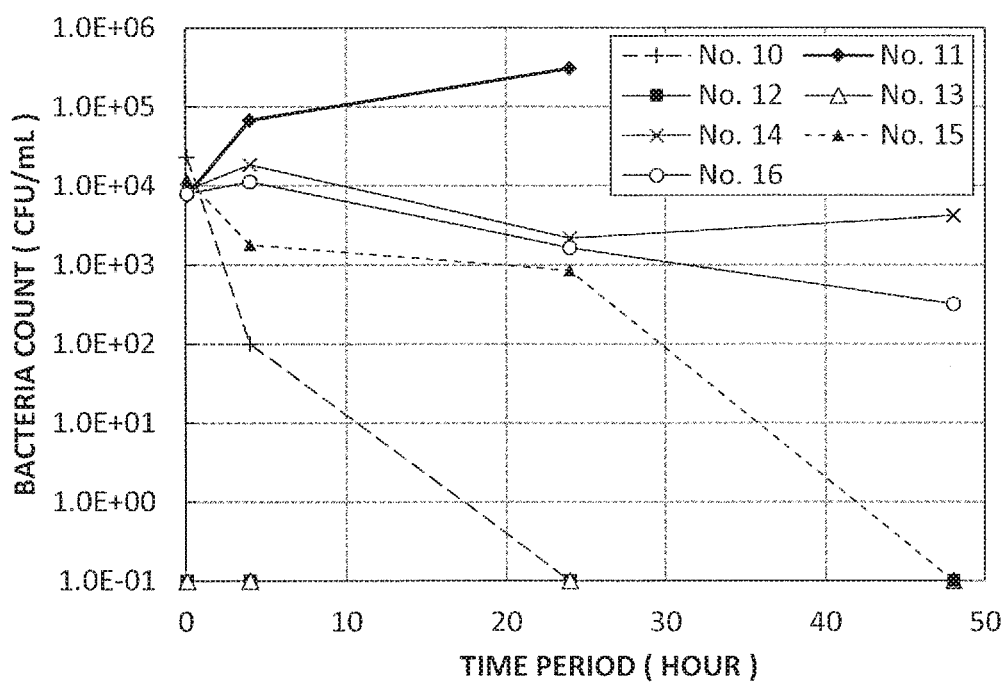
FIG. 7 Graph showing the results of evaluation of the microbicidal ability of sample films No. 10 to No. 16 in experiment 4. The horizontal axis represents the time period for which the samples were left (hour), and the vertical axis represents the bacteria count in bacterial dilution B2 (CFU/mL).

The results are shown in FIG. 7. FIG. 7 is a graph showing the results of evaluation of the microbicidal ability of sample films No. 10 to No. 16 in experiment 4. In FIG. 7, the horizontal axis represents the time period for which the sample films were left (hour), and the vertical axis represents the bacteria count in bacterial dilution B2 (CFU/mL). Note that, in FIG. 7, when the bacteria count is 0, it is plotted as 0.1 for the sake of visibility.

As seen from FIG. 7, sample film No. 10 had a microbicidal ability though it did not include a nitrogen element in the surface of the synthetic polymer film. There may be a probability that the silicone-based lubricant added to the resin had a microbicidal effect for some reasons.

Sample films No. 12 to No. 16 each had a microbicidal ability and/or antimicrobial ability. Particularly, it can be seen that sample films No. 12 and No. 13 which included an amino group (—NH$_2$) had an excellent microbicidal ability. It is estimated that, in sample films No. 12 to No. 16, the functional group included in the silane coupling agent applied to the surface of the synthetic polymer film had a microbicidal effect. Further, in sample films No. 12 to No. 16, a silane coupling agent was applied to the surface of the synthetic polymer film such that the surface of the synthetic polymer film included the nitrogen element in a proportion of not less than 0.7 at %. It is also estimated that the nitrogen element included in the surface of the synthetic polymer film had a microbicidal effect.

On the other hand, sample film No. 11 did not exhibit a microbicidal ability. One of the reasons for this is that no nitrogen element was included in the surface of the synthetic polymer film. It was not found that the vinyl group applied to the surface produced a microbicidal effect. It is seen from comparison between sample film No. 10 and sample film No. 11 that a microbicidal effect was not found because of application of silane coupling agent S0 to the surface of the synthetic polymer film.

Figure 8:
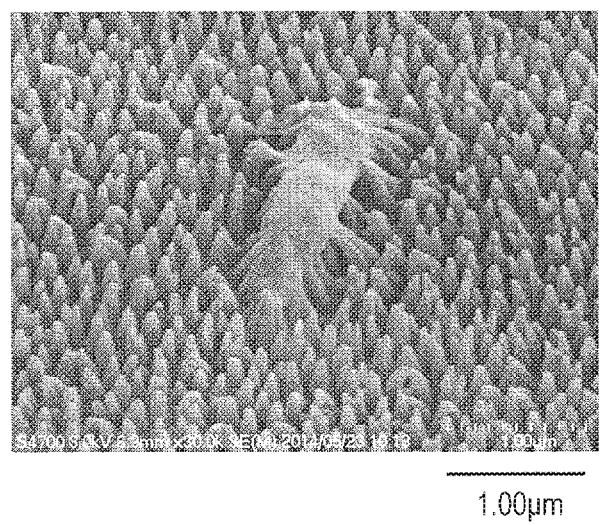
FIGS. 8 (a) and (b) show SEM images obtained by SEM (Scanning Electron Microscope) observation of a *P. aeruginosa* bacterium which died at a surface of sample film No. 10 which had a moth-eye structure.
Figure 8:
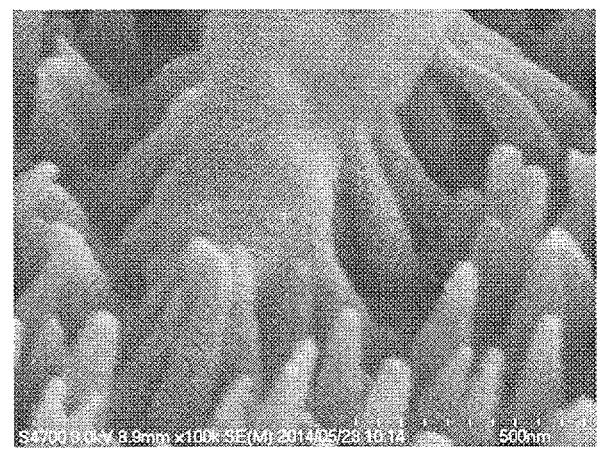

FIGS. 8(*a*) and 8(*b*) show examples of observation by SEM (Scanning Electron Microscope) of a *P. aeruginosa* bacterium which died at the surface of sample film No. 10 which had a moth-eye structure. FIG. 8(*b*) is an enlarged view of FIG. 8(*a*).

As seen from these SEM images, the tip end portions of the raised portions enter the cell wall (exine) of a *P. aeruginosa* bacterium. In FIGS. 8(*a*) and 8(*b*), the raised portions do not appear to break through the cell wall but appears to be taken into the cell wall. This might be explained by the mechanism suggested in the "Supplemental Information" section of Non-patent Document 1. That is, it is estimated that the exine (lipid bilayer) of the Gram-negative bacteria came close to the raised portions and deformed so that the lipid bilayer locally underwent a transition like a first-order phase transition (spontaneous reorientation) and openings were formed in portions close to the raised portions, and the raised portions entered these openings. Alternatively, it is estimated that the raised portions were taken in due to the cell's mechanism of taking a polar substance (including a nutrient source) into the cell (endocytosis).

EXPERIMENT 5

Next, sample films No. 17 and No. 18 shown in Table 2 below were evaluated as to the microbicidal ability.

cidal ability varied depending on the presence/absence of the moth-eye structure over the surface. That is, the synthetic polymer film did not have a microbicidal ability when the surface only included the cyano group, and it is estimated that both the physical structure (moth-eye structure) provided over the surface and the cyano group applied to the surface contributed to the microbicidal ability.

TABLE 2

| NO. | SYNTHETIC POLYMER FILM (BASE FILM: PET) | MOTH-EYE STRUCTURE | SUBSTANCE APPLIED TO SURFACE | FUNCTIONAL GROUP |
|---|---|---|---|---|
| 17 | ACRYLIC RESIN D WITH SILICONE-BASED LUBRICANT ADDED | WITH | CYANOACRYLATE | CYANO GROUP —C≡N |
| 18 | PET | WITHOUT | CYANOACRYLATE | CYANO GROUP —C≡N |

The same substance was applied to the surfaces of sample films No. 17 and No. 18. Sample films No. 17 and No. 18 were different in whether or not they had a moth-eye structure over the surfaces.

Sample film No. 17 was produced using acrylic resin D with a silicone-based lubricant added (which was the same as that used for sample films No. 10 to No. 16 as previously described) with the use of the same mold as that described above. Cyanoacrylate was applied to the surface of a resultant synthetic polymer film. Application of cyanoacrylate was realized by preparing a mixture solution of 1 g instant glue (product name: strong instant glue, importer: Kobunshi Shouji Co. Ltd.) and 50 mL acetone and applying the resultant mixture solution to the surface of the synthetic polymer film in such a manner that the mixture solution flows across the film surface. It was confirmed by observation with a scanning electron microscope (SEM) that the moth-eye structure of the surface was not filled with the mixture solution.

Sample film No. 18 was produced by applying the same mixture solution as that used for sample film No. 17 to the surface of a PET film which was the same as that used as the base film of sample films No. 10 to No. 17. Therefore, sample film No. 18 was the same as sample film No. 17 with respect to the chemical properties of the surface but different from sample film No. 17 in that the surface did not have a moth-eye structure.

The procedure of evaluation of the microbicidal ability was basically the same as that of experiment 1 as described above. In experiment 5, the initial bacteria count for each of the sample films was 3.0E+05 CFU/mL.

Figure 9:
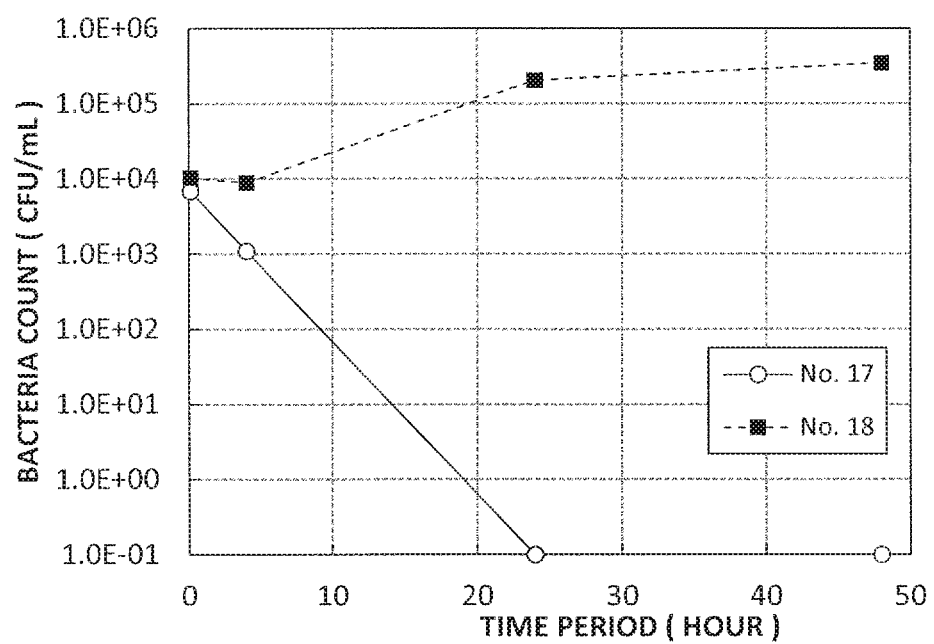
FIG. 9 Graph showing the results of evaluation of the microbicidal ability of sample films No. 17 and No. 18 in experiment 5. The horizontal axis represents the time period for which the samples were left (hour), and the vertical axis represents the bacteria count in bacterial dilution B2 (CFU/mL).

The results are shown in FIG. 9. FIG. 9 is a graph showing the results of evaluation of the microbicidal ability of sample films No. 17 and No. 18 in experiment 5. In FIG. 9, the horizontal axis represents the time period for which the sample films were left (hour), and the vertical axis represents the bacteria count in bacterial dilution B2 (CFU/mL). Note that, in FIG. 9, when the bacteria count is 0, it is plotted as 0.1 for the sake of visibility.

As seen from FIG. 9, sample film No. 17 had a microbicidal ability while sample film No. 18 did not have a microbicidal ability. The presence/absence of the microbi-

EXPERIMENT 6

Next, sample films No. 19 to No. 22 shown in Table 3 below were evaluated as to the microbicidal ability.

TABLE 3

| NO. | SYNTHETIC POLYMER FILM (BASE FILM: PET) |
|---|---|
| 19 | PET |
| 20 | URETHANE ACRYLATE-CONTAINING ACRYLIC RESIN B |
| 21 | URETHANE ACRYLATE-CONTAINING ACRYLIC RESIN B INCLUDING LITHIUM SALT |
| 22 | ACRYLIC RESIN A INCLUDING LITHIUM SALT |

Sample films No. 20 to No. 22 were produced using the same mold as that used in the previously-described experiments. No surface treatment agent was applied to the surfaces of sample films No. 19 to No. 22.

Sample film No. 19 was a PET film which was the same as that used as the base film of sample films No. 20 to No. 22.

Sample film No. 20 was produced using urethane acrylate-containing acrylic resin B (which was the same as that used for sample film No. 2 as previously described).

Sample film No. 21 was produced using a resin which was prepared by adding a silicone oil which included a lithium salt (antistatic agent manufactured by Marubishi Oil Chemical Corporation, product name: PC-3662) to urethane acrylate-containing acrylic resin B which was the same as that used for sample film No. 20.

Sample film No. 22 was produced using a resin which was prepared by adding a silicone oil which included a lithium salt (which was the same as that used for sample film No. 21) to acrylic resin A (which was the same as that used for sample film No. 1 as previously described).

The procedure of evaluation of the microbicidal ability was basically the same as that of experiment 1 as described above. The initial bacteria count for sample films No. 19 and No. 20 was 1.4E+05 CFU/mL. The initial bacteria count for sample film No. 21 was 3.0E+05 CFU/mL. The initial bacteria count for sample film No. 22 was 2.5E+06 CFU/mL.

Figure 10:
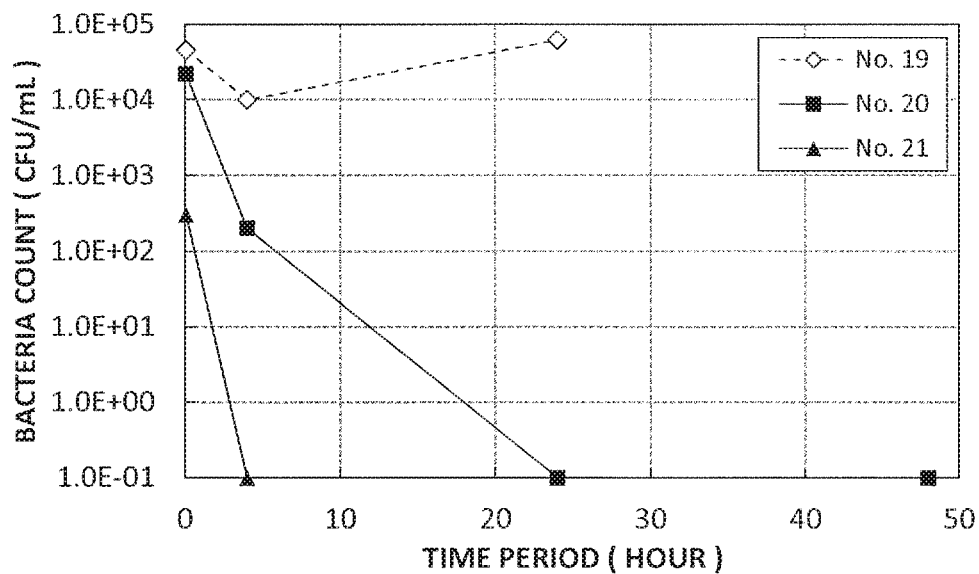
FIG. 10 (a) is a graph showing the results of evaluation of the microbicidal ability of sample films No. 19 to No. 21 in experiment 6. (b) is a graph showing the results of evaluation of the microbicidal ability of sample film No. 22 in experiment 6. In (a) and (b), the horizontal axis represents the time period for which the samples were left (hour), and the vertical axis represents the bacteria count in bacterial dilution B2 (CFU/mL).
Figure 10:
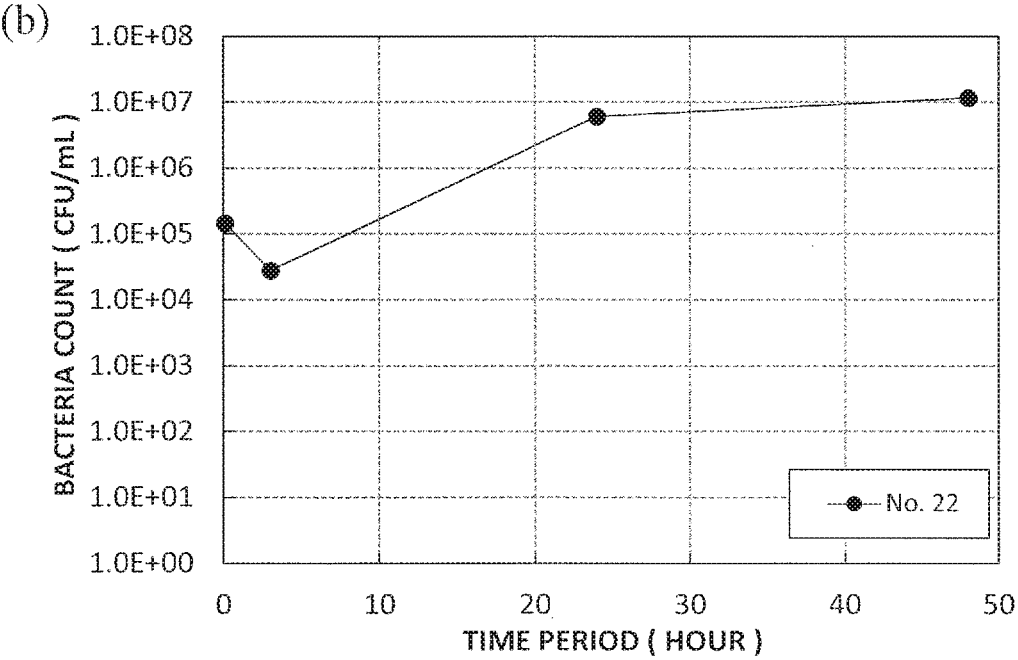

The results are shown in FIGS. 10(a) and 10(b). FIG. 10(a) is a graph showing the results of evaluation of the microbicidal ability of sample films No. 19 to No. 21 in experiment 6. FIG. 10(b) is a graph showing the results of evaluation of the microbicidal ability of sample film No. 22 in experiment 6. In FIG. 10, the horizontal axis represents the time period for which the sample films were left (hour), and the vertical axis represents the bacteria count in bacterial dilution B2 (CFU/mL). Note that, in FIG. 10, when the bacteria count is 0, it is plotted as 0.1 for the sake of visibility.

As seen from FIGS. 10(a) and 10(b), both sample films No. 20 and No. 21 had a microbicidal ability. It is seen from comparison of the results of sample films No. 20 and No. 21 that inclusion of a lithium salt in the synthetic polymer films provides a better microbicidal ability.

Comparing the results of sample films No. 21 and No. 22, it seems that the synthetic polymer film had a microbicidal ability due to inclusion of urethane acrylate. Note that, however, a probability can exist that the microbicidal ability of sample film No. 22 was not sufficiently found in experiment 6 because the initial bacteria count of sample film No. 22 was about 10 times the initial bacteria count of sample film No. 21.

A synthetic polymer film according to an embodiment of the present invention is suitably applicable to uses of suppressing generation of slime on a surface which is in contact with water, for example. For example, the synthetic polymer film is attached onto the inner walls of a water container for a humidifier or ice machine, whereby generation of slime on the inner walls of the container can be suppressed. The slime is attributed to a biofilm which is formed of extracellular polysaccharide (EPS) secreted from bacteria adhering to the inner walls and the like. Therefore, killing the bacteria adhering to the inner walls and the like enables suppression of generation of the slime.

As described above, bringing a liquid into contact with the surface of a synthetic polymer film according to an embodiment of the present invention enables sterilization of the liquid. Likewise, bringing a gas into contact with the surface of a synthetic polymer film according to an embodiment of the present invention enables sterilization of the gas. In general, microorganisms have such a surface structure that they can easy adhere to the surface of an object in order to increase the probability of contact with organic substances which will be their nutrients. Therefore, when a liquid or gas which contains microorganisms is brought into contact with a microbicidal surface of a synthetic polymer film according to an embodiment of the present invention, the microorganisms are likely to adhere to the surface of the synthetic polymer film, and therefore, on that occasion, the liquid or gas is subjected to the microbicidal activity.

Although the microbicidal activity of a synthetic polymer film according to an embodiment of the present invention against *P. aeruginosa* that is a Gram-negative bacteria has been described in this section, the synthetic polymer film has a microbicidal activity not only on Gram-negative bacteria but also on Gram-positive bacteria and other microorganisms. One of the characteristics of the Gram-negative bacteria resides in that they have a cell wall including an exine. The Gram-positive bacteria and other microorganisms (including ones that do not have a cell wall) have a cell membrane. The cell membrane is formed by a lipid bilayer as is the exine of the Gram-negative bacteria. Therefore, it is estimated that the interaction between the raised portions of the surface of the synthetic polymer film according to an embodiment of the present invention and the cell membrane is basically the same as the interaction between the raised portions and the exine.

Note that, however, the size of the microorganisms varies depending on their types. The size of *P. aeruginosa* which has been described herein as an example is about 1 μm. However, the size of the bacteria ranges from several hundreds of nanometers to about five micrometers. The size of fungi is not less than several micrometers. It is estimated that the raised portions of the synthetic polymer film which has been described above (the two-dimensional size is about 200 nm) have a microbicidal activity on a microorganism whose size is not less than about 0.5 μm, but there is a probability that the raised portions are too large to exhibit a sufficient microbicidal activity on a bacterium whose size is several hundreds of nanometers. The size of viruses ranges from several tens of nanometers to several hundreds of nanometers, and many of them have a size of not more than 100 nm. Note that viruses do not have a cell membrane but have a protein shell called capsid which encloses virus nucleic acids. The viruses can be classified into those which have a membrane-like envelope outside the shell and those which do not have such an envelope. In the viruses which have an envelope, the envelope is mainly made of a lipid. Therefore, it is expected that the raised portions likewise act on the envelope. Examples of the viruses which have an envelope include influenza virus and Ebola virus. In the viruses which do not have an envelope, it is expected that the raised portions likewise act on this protein shell called capsid. When the raised portions include nitrogen element, the raised portions can have an increased affinity for a protein which is made of amino acids.

In view of the above, the configuration and production method of a synthetic polymer film having raised portions which can exhibit a microbicidal activity against a microorganism of not more than several hundreds of nanometers are described below.

In the following description, raised portions of the above-described synthetic polymer film which have a two-dimensional size in the range of more than 20 nm and less than 500 nm are referred to as "first raised portions". Raised portions which are superimposedly formed over the first raised portions are referred to as "second raised portions". The two-dimensional size of the second raised portions is smaller than the two-dimensional size of the first raised portions and does not exceed 100 nm. Note that when the two-dimensional size of the first raised portions is less than 100 nm, particularly less than 50 nm, it is not necessary to provide the second raised portions. Recessed portions of the mold corresponding to the first raised portions are referred to as "first recessed portions", and recessed portions of the mold corresponding to the second raised portions are referred to as "second recessed portions".

When the method of forming the first recessed portions which have predetermined size and shape by alternately performing the anodization step and the etching step as described above is applied without any modification, the second recessed portions cannot be formed successfully.

Figure 11:
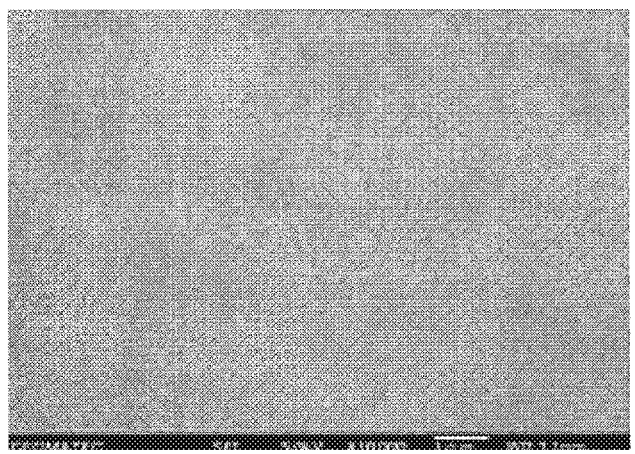
FIG. 11 (a) shows a SEM image of a surface of an aluminum base. (b) shows a SEM image of a surface of an aluminum film. (c) shows a SEM image of a cross section of the aluminum film.
Figure 11:
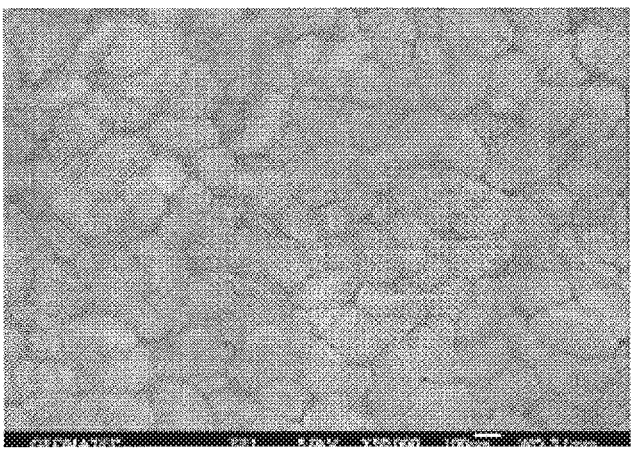
Figure 11:
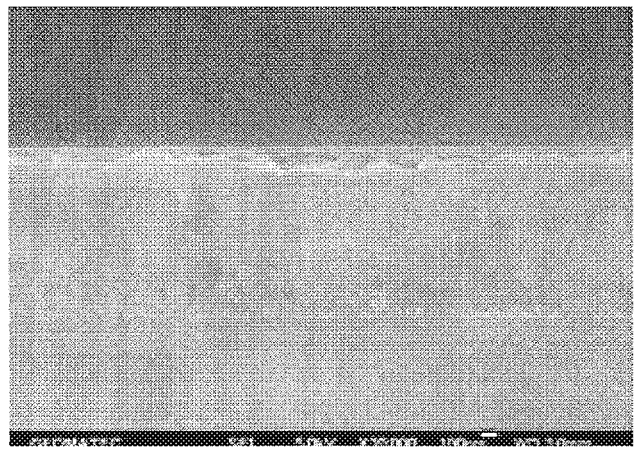

FIG. 11(a) shows a SEM image of a surface of an aluminum base (designated by reference numeral 12 in FIG. 2). FIG. 11(b) shows a SEM image of a surface of an aluminum film (designated by reference numeral 18 in FIG. 2). FIG. 11(c) shows a SEM image of a cross section of the aluminum film (designated by reference numeral 18 in FIG. 2). As seen from these SEM images, there are grains (crystal grains) at the surface of the aluminum base and the surface of the aluminum film. The grains of the aluminum film form unevenness at the surface of the aluminum film. This unevenness at the surface affects formation of the recessed portions in the anodization and therefore interrupts formation of second recessed portions whose $D_p$ or $D_{int}$ is smaller than 100 nm.

In view of the above, a mold manufacturing method according to an embodiment of the present invention includes: (a) providing an aluminum base or an aluminum film deposited on a support; (b) the anodization step of applying a voltage at the first level while a surface of the aluminum base or aluminum film is kept in contact with an electrolytic solution, thereby forming a porous alumina layer which has the first recessed portions; (c) after step (b), the etching step of bringing the porous alumina layer into contact with an etching solution, thereby enlarging the first recessed portions; and (d) after step (c), applying a voltage at the second level that is lower than the first level while the porous alumina layer is kept in contact with an electrolytic solution, thereby forming the second recessed portions in the first recessed portions. For example, the first level is higher than 40 V, and the second level is equal to or lower than 20 V.

Specifically, an anodization step is carried out with the voltage at the first level, whereby the first recessed portions are formed which have such a size that is not influenced by the grains of the aluminum base or aluminum film. Thereafter, the thickness of the barrier layer is decreased by etching, and then, another anodization step is carried out with the voltage at the second level that is lower than the first level, whereby the second recessed portions are formed in the first recessed portions. When the second recessed portions are formed through such a procedure, the influence of the grains is avoided.

Figure 12:
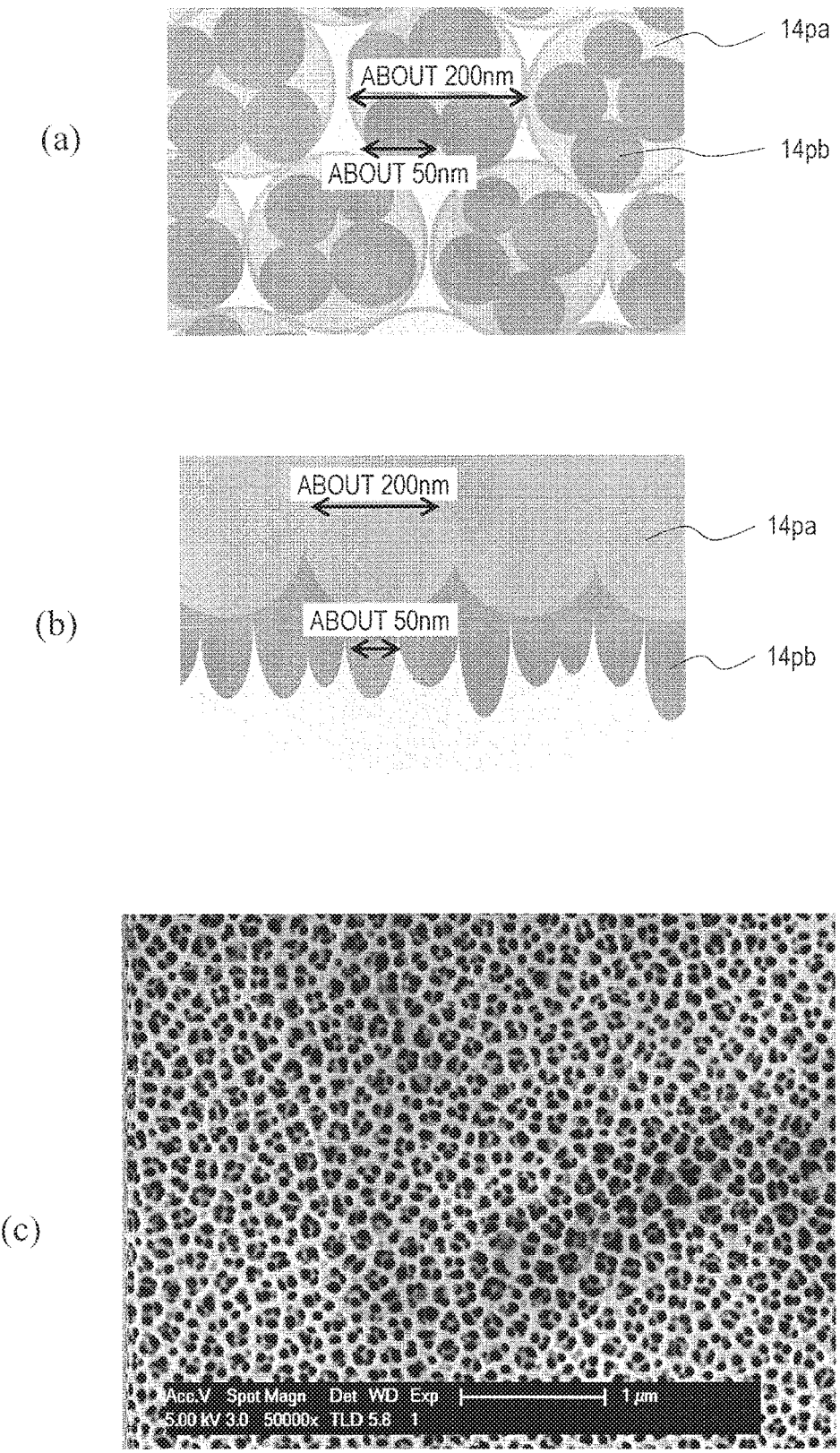
FIG. 12 (*a*) is a schematic plan view of a porous alumina layer of a mold. (*b*) is a schematic cross-sectional view of the porous alumina layer. (*c*) is a SEM image of a prototype mold.

A mold which has first recessed portions 14$pa$ and second recessed portions 14$pb$ formed in the first recessed portions 14$pa$ is described with reference to FIG. 12. FIG. 12($a$) is a schematic plan view of a porous alumina layer of a mold. FIG. 12($b$) is a schematic cross-sectional view of the porous alumina layer. FIG. 12($c$) shows a SEM image of a prototype mold.

As shown in FIGS. 12($a$) and 12($b$), the surface of the mold of the present embodiment has the plurality of first recessed portions 14$pa$ whose two-dimensional size is in the range of more than 20 nm and less than 500 nm and the plurality of second recessed portions 14$pb$ which are superimposedly formed over the plurality of first recessed portions 14$pa$. The two-dimensional size of the plurality of second recessed portions 14$pb$ is smaller than the two-dimensional size of the plurality of first recessed portions 14$pa$ and does not exceed 100 nm. The height of the second recessed portions 14$pb$ is, for example, more than 20 nm and not more than 100 nm. The second recessed portions 14$pb$ preferably have a generally conical portion as do the first recessed portions 14$pa$.

The porous alumina layer shown in FIG. 12($c$) was formed as described below.

The aluminum film used was an aluminum film which contains Ti at 1 mass %. The anodization solution used was an oxalic acid aqueous solution (concentration: 0.3 mass %, solution temperature: 10° C.). The etching solution used was a phosphoric acid aqueous solution (concentration: 10 mass %, solution temperature: 30° C.). After the anodization was carried out with a voltage of 80 V for 52 seconds, the etching was carried out for 25 minutes. Then, the anodization was carried out with a voltage of 80 V for 52 seconds, and the etching was carried out for 25 minutes. Thereafter, the anodization was carried out with a voltage of 20 V for 52 seconds, and the etching was carried out for 5 minutes. Further, the anodization was carried out with a voltage of 20 V for 52 seconds.

As seen from FIG. 12($c$), the second recessed portions whose $D_p$ was about 50 nm were formed in the first recessed portions whose $D_p$ was about 200 nm. When in the above-described manufacturing method the voltage at the first level was changed from 80 V to 45 V for formation of the porous alumina layer, the second recessed portions whose $D_p$ was about 50 nm were formed in the first recessed portions whose $D_p$ was about 100 nm.

When a synthetic polymer film is produced using such a mold, the produced synthetic polymer film has raised portions whose configuration is the inverse of that of the first recessed portions 14$pa$ and the second recessed portions 14$pb$ shown in FIGS. 12($a$) and 12($b$). That is, the produced synthetic polymer film further includes a plurality of second raised portions superimposedly formed over a plurality of first raised portions.

The thus-produced synthetic polymer film which has the first raised portions and the second raised portions superimposedly formed over the first raised portions has a microbicidal activity on various microorganisms, ranging from relatively small microorganisms of about 100 nm to relatively large microorganisms of not less than 5 μm.

As a matter of course, only raised portions whose two-dimensional size is in the range of more than 20 nm and less than 100 nm may be formed according to the size of a target microorganism. The mold for formation of such raised portions can be manufactured, for example, as described below.

The anodization is carried out using a neutral salt aqueous solution (ammonium borate, ammonium citrate, etc.), such as an ammonium tartrate aqueous solution, or an organic acid which has a low ionic dissociation degree (maleic acid, malonic acid, phthalic acid, citric acid, tartaric acid, etc.) to form a barrier type anodized film. After the barrier type anodized film is removed by etching, the anodization is carried out with a predetermined voltage (the voltage at the second level described above), whereby recessed portions whose two-dimensional size is in the range of more than 20 nm and less than 100 nm can be formed.

For example, an aluminum film which contains Ti at 1 mass % is anodized at 100 V for 2 minutes using a tartaric acid aqueous solution (concentration: 0.1 mol/l, solution temperature: 23° C.), whereby a barrier type anodized film is formed. Thereafter, the etching is carried out for 25 minutes using a phosphoric acid aqueous solution (concentration: 10 mass %, solution temperature: 30° C.), whereby the barrier type anodized film is removed. Thereafter, the anodization and the etching are alternatively repeated as described above, specifically through 5 anodization cycles and 4 etching cycles. The anodization was carried out at 20 V for 52 seconds using an oxalic acid aqueous solution (concentration: 0.3 mass %, solution temperature: 10° C.) as the anodization solution. The etching was carried out for 5 minutes using the above-described etching solution. As a result, recessed portions whose two-dimensional size is about 50 nm can be uniformly formed.

INDUSTRIAL APPLICABILITY

A synthetic polymer film which has a microbicidal surface according to an embodiment of the present invention is applicable to various uses including, for example, uses for sterilization of surfaces of kitchen and bathroom facilities. The synthetic polymer film which has a microbicidal surface according to an embodiment of the present invention can be produced at low cost.

REFERENCE SIGNS LIST 34A, 34B synthetic polymer film
34A$p$, 34B$p$ raised portions 42A, 42B base film
50A, 50B film
100, 100A, 100B moth-eye mold

The invention claimed is:

1. A synthetic polymer film having a surface which comprises
a plurality of first raised portions, wherein a two-dimensional size of the plurality of first raised portions is in a range of more than 20 nm and less than 500 nm when viewed in a normal direction of the synthetic polymer film; and
a plurality of second raised portions superimposedly formed over the plurality of first raised portions, wherein a two-dimensional size of the plurality of second raised portions is smaller than the two-dimensional size of the plurality of first raised portions and does not exceed 100 nm;
the plurality of first raised portions include a first raised portion that has two or more of the second raised portions; and
wherein the surface has a microbicidal effect, and
a concentration of a nitrogen element included in the surface is not less than 0.7 at %.

2. The synthetic polymer film of claim 1, produced from a urethane acrylate-containing acrylic resin.

3. The synthetic polymer film of claim 1, comprising any of an amino group, an isocyanate group and a cyano group.

4. The synthetic polymer film of claim 1, wherein the synthetic polymer film is made from a compound whose terminal functional group includes $-NH_2$ or $-NHR$, wherein R represents a hydrocarbon group.

5. The synthetic polymer film of claim 1, further comprising a silane coupling agent, wherein the coupling agent includes any of an amino group, an isocyanate group and a cyano group.

6. The synthetic polymer film of claim 5, wherein the silane coupling agent is present in or on the surface of the synthetic polymer film.

7. The synthetic polymer film of claim 1, further comprising an alkali metal salt or an alkali earth metal salt.

8. The synthetic polymer film of claim 1, further comprising a lithium salt.

9. The synthetic polymer film of claim 1, wherein the plurality of first raised portions include a conical portion.

* * * * *